United States Patent [19]

Vincenti et al.

[11] Patent Number: 5,202,115
[45] Date of Patent: Apr. 13, 1993

[54] BASIC ALUMINUM ANTIPERSPIRANT ACTIVE MATERIAL HAVING ENHANCED ACTIVITY, ANTIPERSPIRANT ACTIVE COMPOSITION CONTAINING SUCH MATERIAL, AND METHODS FOR PREPARATION OF SUCH MATERIAL AND COMPOSITION

[75] Inventors: Paul J. Vincenti, Jefferson; Morton L. Barr, Rockaway, both of N.J.

[73] Assignee: The Mennen Company, Morristown, N.J.

[21] Appl. No.: 518,516

[22] Filed: May 2, 1990

Related U.S. Application Data

[63] Continuation-in-part of Ser. No. 233,008, Aug. 17, 1988, abandoned.

[51] Int. Cl.$^5$ .......................... A61K 7/38; A61K 7/34
[52] U.S. Cl. ........................ 424/66; 424/68; 423/600; 423/625
[58] Field of Search ..................... 424/68, 66

[56] References Cited

U.S. PATENT DOCUMENTS

| | | | |
|---|---|---|---|
| 4,223,010 | 9/1980 | Rubino et al. | 424/66 |
| 4,775,528 | 10/1988 | Callaghan et al. | 424/66 X |
| 4,871,525 | 10/1989 | Giovanniello et al. | 424/66 X |
| 4,900,534 | 2/1990 | Inward | 424/66 X |

FOREIGN PATENT DOCUMENTS

39560/89  8/1988  Australia.

OTHER PUBLICATIONS

Teagarden et al., "J. of Pharm. Sci.," 70, No. 7 (Jul. 1981), pp. 762–764.

*Primary Examiner*—Paul F. Shaver
*Attorney, Agent, or Firm*—Antonelli, Terry, Stout & Kraus

[57] ABSTRACT

Disclosed is a basic aluminum material having enhanced antiperspirant activity, the material having the empirical formula $Al_2(OH)_{6-a}X_a$, where $0.5 \leq a \leq 5.0$ and X is a univalent complex oxoanion of nitrogen, chlorine and other halogens, which forms salts with $Al^{3+}$ in aqueous solution so that these salts are essentially completely dissociated, which is readily soluble in water with metallic ions in the solution, and which forms conjugate acids that are strong acids; and wherein the material is characterized by:

(a) size exclusion high performance liquid chromatography peaks corresponding to peak 3 and peak 4 of size exclusion chromatograms formed by HPLC technique;

(b) a peak 4 relative area of at least 25%, a peak 3 relative area of less than 60%, the sum of the relative peak 3 and peak 4 areas being at least 50%; and (c) less than 10% chromatographic peaks eluting at shorter retention times than peak 3, corresponding to peaks 1 and 2.

25 Claims, 24 Drawing Sheets

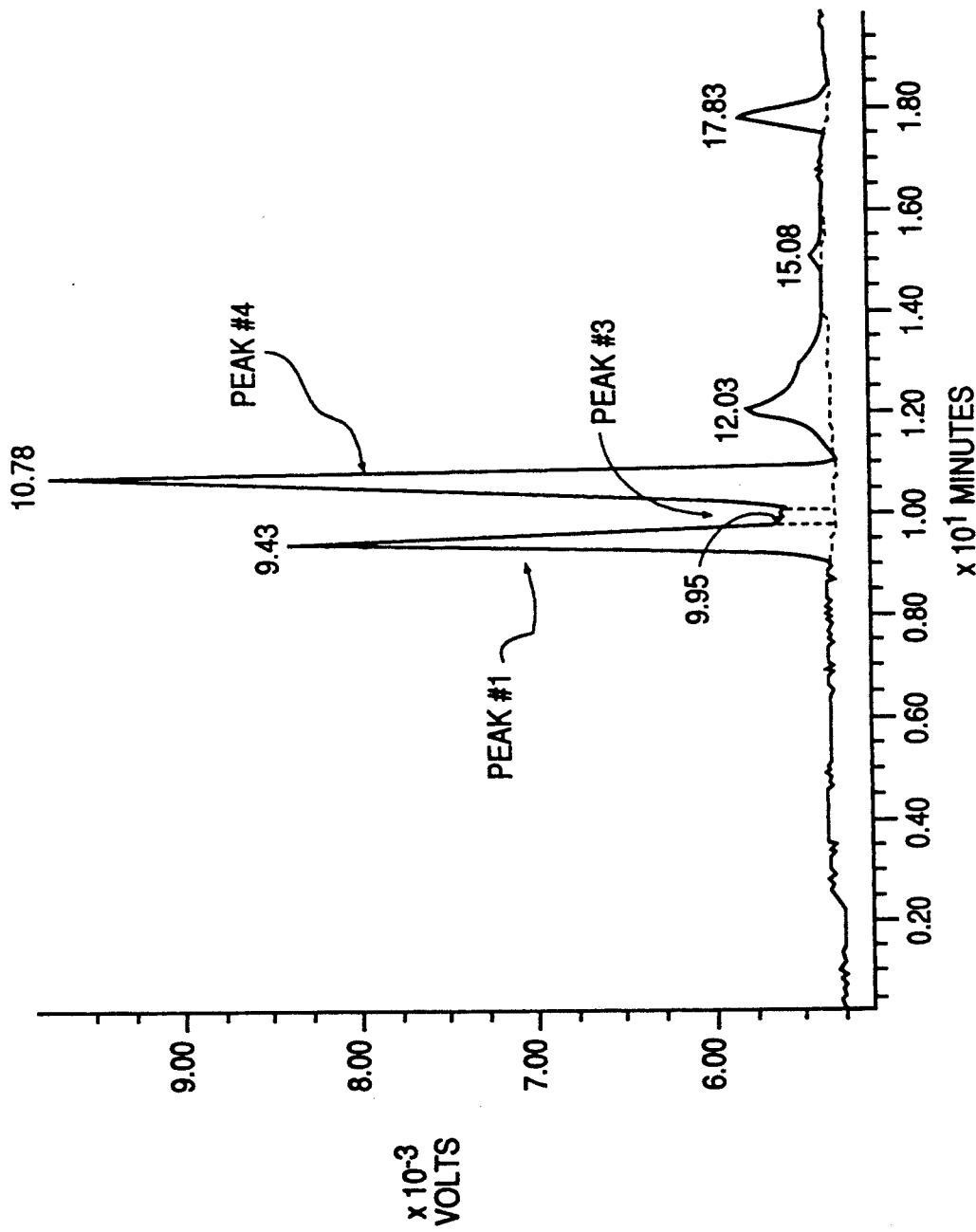

BASIC ALUMINUM ANTIPERSPIRANT ACTIVE MATERIAL HAVING ENHANCED ACTIVITY, ANTIPERSPIRANT ACTIVE COMPOSITION CONTAINING SUCH MATERIAL, AND METHODS FOR PREPARATION OF SUCH MATERIAL AND COMPOSITION

This application is a continuation-in-part application of Ser. No. 07/233,008, filed Aug. 17, 1988, now abandoned, the contents of which is incorporated herein in its entirety.

BACKGROUND OF THE INVENTION

The present invention relates to basic aluminum antiperspirant active materials having enhanced antiperspirant activity, antiperspirant active compositions including such basic aluminum antiperspirant active materials and also containing zirconium, hafnium, titanium and/or tin antiperspirant active materials, and methods of producing such materials and compositions. Moreover, the present invention is directed to basic aluminum antiperspirant active materials (polymeric species of basic aluminum compounds) and antiperspirant active compositions containing such materials, having enhanced antiperspirant activity, which can be produced under conditions much less severe than those utilized in producing conventional basic aluminum materials and compositions with enhanced antiperspirant activity, and which are more stable in aqueous solution than conventional basic aluminum materials and compositions having enhanced antiperspirant efficacy. The materials and compositions of the present invention have a wide range of application as antiperspirant materials, including, for example, as antiperspirant materials in aerosols, roll-ons, solid stick antiperspirants, etc.

It has been desired to provide improved antiperspirant active materials, having enhanced antiperspirant activity. British Patent Specification No. 1,568,831 describes enhanced efficacy antiperspirant materials, employing certain basic aluminum chloride, bromide, iodide and nitrate compounds, with modification of such compounds in aqueous solution such that the materials include aqueous solutions of polymeric species (of such compounds) having a size greater than 100 Å, in which species having a size greater than 100 Å there is contained from 2-80% by weight of the total aluminum in solution. This British patent discloses that the basic aluminum compound may have the empirical formula $Al_2(OH)_{6-a}X_a$, where X is Cl, Br, I or $NO_3$ and a is from 0.4 to 1.5. This patent discloses that the modified basic aluminum compounds which in aqueous solution contain polymeric species having a size greater than 100 Å may be prepared by heating aqueous solutions of the basic aluminum compounds at elevated temperatures, preferably 80° C. to 140° C., for periods of 0.5 hour to 30 days (the period of heating being shorter at higher temperatures).

In Example 14 of this British patent, there is disclosed preparation of a basic aluminum nitrate to form the disclosed enhanced efficacy antiperspirant materials. Specifically, an aluminum nitrate nonahydrate solution was prepared and then heated to 90° C. under a reflux condenser, with aluminum powder being added in small portions and heating then being continued with stirring; thereafter, the solution was cooled to room temperature and filtered to remove excess aluminum, so as to provide the described aqueous solutions of the basic aluminum nitrate. The contents of British Patent Specification No. 1,568,831 are incorporated herein by reference in their entirety.

While British Patent Specification No. 1,568,831 discloses modified nitrate-containing basic aluminum compounds having enhanced antiperspirant activity, this patent focuses on modified compounds which form polymer species of a size greater than 100 Å in aqueous solution. Moreover, in the example utilizing basic aluminum nitrate, heating is performed at relatively high temperatures of 90° C. and for relatively long time periods of 29 hours. Neither the compounds or methods disclosed in this British Patent Specification No. 1,568,831 achieves the objectives of the present invention.

U.S. Pat. No. 4,359,456 discloses an improved antiperspirant active material, and methods for its preparation, the material comprising a polymeric aluminum compound having the empirical formula $Al_2(OH)_{6-a}X_a$, wherein X is Cl, Br or I, a is about 0.3 to about 4, and wherein the antiperspirant active material is further characterized by: (a) a Size Exclusion Chromatography Test band having a relative retention time corresponding to Band III of the Standard Basic Aluminum Chloride Solution Size Exclusion Chromatogram; and (b) a Band III Percent Aluminum Value of at least 20%. This patent discloses that the enhanced antiperspirant effectiveness is related to the presence of a particular band (Band III) detected in the Size Exclusion Chromatography test, and that enhancement of the antiperspirant activity of the basic aluminum halide compounds having the empirical formula $Al_2(OH)_{6-a}X_a$ is achieved by increasing the aluminum content in the Band III fraction.

This U.S. Pat. No. 4,359,456 specifies that the basic aluminum halide compounds can be modified to provide enhanced activity antiperspirant materials by heating aqueous solutions of the basic aluminum halide compounds at elevated temperatures. Specifically, this patent discloses heating the aqueous solutions at temperatures of from 50° C. to 140° C., the period of heating being for periods of 0.5 hour to 30 days, depending on the temperature used (the period of heating being shorter when high temperatures are used). This patent also discloses that the concentration of the basic aluminum compound in the solution is important, with the aluminum concentration of the solution of the basic aluminum compound to be treated ranging from 2.5% to 8.5% by weight. This U.S. Pat. No. 4,359,456 additionally specifies that the aqueous solution of the enhanced activity antiperspirant compound comprising the Band III polymeric species may, if desired, be dried to give the compound the form of a solid hydrate, and that spray-drying may be a particularly useful method for such drying to provide the solid hydrate. This patent further discloses that the enhanced activity antiperspirant material described therein can be incorporated with various materials, such as a perfume, thickener, alcohol or propellant, to provide antiperspirant compositions. The contents of U.S. Pat. No. 4,359,456, including the description therein of various materials with which the modified, antiperspirant active compound can be combined to provide antiperspirant compositions, are incorporated herein by reference in their entirety.

While U.S. Pat. No. 4,359,456 discloses basic aluminum halide compounds treated to provide materials having enhanced antiperspirant activity, such technique described therein has various disadvantages. Initially, the enhanced antiperspirant active material disclosed therein is relatively unstable in concentrated aqueous solution, and loses its enhanced efficacy in relatively short periods of time. Furthermore, this patent discloses that a desirable heating temperature for modifying the basic aluminum halides is upwards of 140° C.; as can be appreciated, the relatively high heating temperature increases the cost of manufacturing the antiperspirant. Moreover, since the process of this patent includes an additional manufacturing step of heating a previously manufactured commercial antiperspirant, this process decreases throughput and, therefore, increases manufacturing costs.

European Patent Application No. 183,171 describes a method of preparing an enhanced efficacy aluminum chlorhydrate antiperspirant active material, the aluminum chlorhydrate material formed, and antiperspirant compositions containing such aluminum chlorhydrate, wherein an aqueous solution containing about 40–50 wt. % of aluminum chlorhydrate is heated to a temperature of at least about 130° C. for about one to twelve hours (the heating time being inversely proportional to temperature) in a closed vessel, and cooling the resulting product, to provide the aluminum chlorhydrate having enhanced antiperspirant activity. The aluminum chlorhydrate treated according to the disclosed method is represented by the empirical formula $Al_2(OH)_{6-x}Cl_x$, wherein x is in the range of about 1 to 2. This European patent application discloses that the modified aluminum chlorhydrate having enhanced antiperspirant activity, formed as indicated herein, is characterized by a size exclusion chromatogram having a single major peak with a relative retention time at its apex of about 0.75–0.79, with the area under the peak indicating at least 60% of the aluminum-containing species is within the fraction represented by the major peak. This European patent application further discloses that the resulting aluminum chlorhydrate solid, after the described heat-treatment and drying, may be incorporated into various conventional antiperspirant forms such as solutions (aqueous, non-aqueous or alcoholic), aerosols, powders, sticks, lotions, roll-ons, gels, creams and the like, which may contain a variety of non-toxic, dermatologically acceptable moieties such as solvents, emollients, propellants, perfumes, etc.

This European Patent Application No. 183,171 describes aluminum chlorhydrate materials having enhanced antiperspirant activity, being formed by heating previously manufactured aluminum chlorhydrate, wherein it is disclosed that the preferred heating temperatures are relatively high temperatures. Furthermore, the enhanced active materials disclosed therein are relatively unstable in concentrated aqueous solution, and lose their enhanced efficacy in relatively short periods of time in solution. Moreover, relatively long periods of heating are required to achieve the enhanced antiperspirant active materials.

European Patent Application No. 191,628 discloses a process for preparing basic aluminum halides having good antiperspirant activities, wherein the aluminum: halogen molar ratio is from 1.7 to 2.2:1 and wherein at least 20% of the aluminum is contained in the Band III fraction, including (a) dissolving metallic aluminum in an aqueous starting solution of an aluminum compound selected from aluminum chloride and aluminum bromide, the starting solution being held at a temperature of about 50° C. to about 105° C. for a time just long enough to dissolve sufficient aluminum to produce an aqueous solution of a final basic aluminum halide having an aluminum: halide molar ratio in the range of 1.7:1 to 2.2:1, the concentration of the aluminum in the starting solution and the amount of aluminum dissolved being such that the aluminum concentration in the solution of the final basic aluminum halide is from 0.8% to about 6.75% by weight and the final basic aluminum halide has at least 20% of the aluminum contained in the Band III fraction; and (b) drying the solution of the final basic aluminum halide so as to give the final basic aluminum halide in the form of a hydrated powder having at least 20% of the aluminum contained in the Band III fraction. This European patent application further describes that an essential feature of the process is the use of proportions of reactants such that when the desired basic aluminum halide is formed, usually at the point when substantially all of the aluminum has dissolved, the aluminum concentration of that solution is relatively low and in the range 0.8% to 6.75% by weight. This patent application specifies that the reaction is most conveniently carried out at atmospheric pressure, although elevated pressures, for example, can be used.

In achieving the range of aluminum concentration of the desired basic aluminum halide, this European Patent Application No. 191,628 describes a process in which the aluminum concentration in the solution, prior to addition of metallic aluminum, is less than 1.0% and in which initial aluminum solution concentrations of 2.0% are not useful. Furthermore, the enhanced antiperspirant active materials disclosed therein are relatively unstable in concentrated aqueous solution, and lose their enhanced efficacy in solution in relatively short periods of time.

Aluminum antiperspirant active materials which are commercially available and which have been disclosed in the prior art, including improved antiperspirant active materials having enhanced antiperspirant activity, typically contain 75–95% $Al^c$, 0–15% $Al^b$ and 0–15% $Al^a$. In one embodiment of European Patent Application No. 191,628, an $Al_{13}O_{40}$ polymeric species is disclosed which may (or may not) complex with the ferron reagent at a rate which is characteristic of $Al^b$. In any case, the formation of $Al_{13}O_{40}$ polymeric species is favored by lower temperatures and shorter reaction times, these shorter reaction times requiring the use of more reactive forms of aluminum metal, such as powders of high surface area, and the use of catalysts.

While each of the European Patent Application Nos. 183,171 and 191,628 are described as advances beyond the technique disclosed in U.S. Pat. No. 4,359,456, neither of the techniques or products disclosed in these European patent applications achieve the benefits of the present invention.

U.K. Patent Application No. 2,048,229 describes a group of complexes, referred to as $Al^{c'}$, which fall within the aluminum chlorhydroxides represented by the empirical formula $Al_2(OH)_5Cl$, which is more efficacious as an antiperspirant. This U.K. Patent Application No. 2,048,229 discloses that the group of complexes is characterized by a diffusion constant in gel permeation chromatography characteristic of complexes of lower molecular sizes, referred to as $Al^b$, and by reaction rates of complexation with a ferron reagent characteristic of complexes of the largest molecular sizes, referred to as $Al^c$. This U.K. Patent Application No. 2,048,229 describes a method for aging presently available aluminum chlorhydroxide in an aqueous medium until the aluminum chlorhydroxide contains at least 45% of the $Al^c$ group.

While U.K. Patent Application No. 2,048,229 discloses a basic aluminum chloride compound treated to provide material having enhanced antiperspirant activity, such material has the disadvantage of requiring relatively long aging periods or low concentrations for its preparation; as can be appreciated, the requirement of aging a previously manufactured basic aluminum chloride for relatively long time periods increases the cost of manufacturing the antiperspirant. Furthermore, this U.K. Patent Application No. 2,048,229 discloses that concentrated solutions of $Al^c$ are not stable for extended periods. Neither the compounds or methods disclosed in this U.K. Patent Application No. 2,048,229 achieve the objectives of the present invention.

All the foregoing documents, apart from British patent specification No. 1,568,831, are directed to halide-containing aluminum materials, and do not disclose basic aluminum materials containing nitrates or other, univalent oxoanions. Moreover, as indicated in the foregoing, each of these materials have disadvantages and do not achieve the objectives of the present invention.

U.S. Pat. No. 4,859,446 to Abrutyn, et al discloses a process for preparing basic aluminum materials having the empirical formula $Al_2(OH)_{6-a}X_a$, where a is about 1.0 to about 4, and X is Cl, Br, I, $SO_4$ or $NO_2$, with the materials having a Band III aluminum value of at least 40%, and preferably having a Band I value of not greater than 5%. The process includes reacting an aqueous solution of an aluminum compound of the empirical formula $Al_nX_m$, where n is 1 or 2 and m is 1 or 3, with aluminum metal at a temperature between 50° and 195° C., until a specific ratio of aluminum to anion is achieved. No mention is made of nitrate-containing basic aluminum material, or of any other univalent oxoanion (other than nitrite). Furthermore, the nitrite essentially forms no salts with $Al^{3+}$ in aqueous solution. Moreover, while this patent discloses use of nitrous acid to produce the basic aluminum nitrite, no mention is made of utilizing nitric acid to produce a basic aluminum nitrate. The compounds according to this U.S. patent cannot achieve the objectives of the present invention.

Furthermore, it is also desired, as part of the present invention, to achieve an antiperspirant composition including an enhanced activity aluminum material and a zirconium, hafnium, tin and/or titanium antiperspirant material, which composition has good stability in aqueous solution and which can be manufactured without utilizing severe processing conditions (for example, without high temperatures and without high pressure conditions).

British Patent Specification No. 1,353,916 discloses aerosol antiperspirant powder spray compositions containing a powder antiperspirant active complex, formed by the steps of: (a) heating an aqueous solution containing from 1 to 3.2 parts by weight of aluminum chlorhydroxide to a temperature of from 190° F. to 225° F.; (b) adding an aqueous solution containing one part by weight of zirconyl hydroxychloride to the aluminum chlorhydroxide solution at such a rate that the addition takes from two hours to five hours, while heating and agitating, the total anhydrous solids content when all of the zirconyl hydroxychloride has been added being at least 19% by weight; and (c) heating and agitating the aluminum chlorhydroxide/zirconyl hydroxychloride mixture at from 190° F. to 225° F. for from one-half hour to about five hours until a stable complex forms. This patent discloses that after forming the stable complex, the complex is dried to an impalpable powder. This patent discloses that the described process results in the production of a higher pH antiperspirant complex (for the same zirconium level as other materials) which is less irritating to the skin, less damaging to fabrics and less corrosive to packaging than conventional compositions; and that the complex also eliminates the need for the addition of buffering, anti-gelling and compatibilizer agents. This patent goes on to state that the dried powder can be incorporated in various powder aerosol antiperspirant compositions as the active material.

U.S. Pat. No. 4,223,010 discloses basic zirconium complexes, used in antiperspirants, formed by reacting acidic aluminum and/or zirconium compounds with a freshly prepared basic zirconium compound selected from basic zirconium-amino acid gels, zirconium hydroxide gels, basic zirconium carbonate gels and mixtures thereof, to form a complex having an Al/Zr molar ratio of about 10:1 to 1:10; this patent discloses that the complexes may be dried to a powder form and used in any of a wide variety of conventional antiperspirant forms, including lotions, creams, roll-ons, aerosol sprays and powder-in-oil aerosol sprays. This patent discloses that the acid aluminum compounds include aluminum halides, as well as other basic aluminum salts such as the nitrates, sulfamates, sulfates and mixtures thereof.

United Kingdom Patent Application No. 2,144,992 discloses a composition of zirconyl hydroxychloride and aluminum chlorhydroxide in stable solid form, having enhanced antiperspirant efficacy when dissolved in water, the composition being made by heating a 2-20% by weight aqueous solution of zirconyl hydroxychloride and aluminum chlorhydroxide at a temperature of at least 50° C. until the ratio of the height of peak 4 to that of peak 3, as measured by gel permeation chromatography on cross-linked dextran, exceeds 2:1, then subjecting the solution to rapid drying to solid form. This United Kingdom patent application further discloses that the inclusion in the composition of a neutral amino acid does not have an adverse affect upon the formation of the desired complex, and does not interfere with the conversion of the heated solution to solid form nor with subsequent use of the solids as an antiperspirant. This United Kingdom patent application further discloses that the neutral amino acid (for example, glycine) aids in preventing gelation of the aqueous solution before or during the heating step.

Each of British Patent Specification No. 1,353,916 and British U.K. Patent Application No. 2,144,992 is directed to compositions including aluminum chlorhydroxide. Moreover, while U.S. Pat. No. 4,223,010 discloses use of various basic aluminum compounds, there is no disclosure that the aluminum has enhanced activity. Similarly, there is no disclosure in British Patent Specification No. 1,353,916 that the basic aluminum compound has enhanced activity. None of the compositions and methods disclosed in British Patent Specification No. 1,353,916, British Patent Application No. 2,144,992 and U.S. Pat. No. 4,223,010 achieves the objectives of the present invention.

U.S. Pat. No. 4,331,609 discloses antiperspirant aluminum and zirconium complexes including an aluminum compound, a zirconium compound, a neutral amino acid and an inorganic acidic compound. The aluminum compound has the empirical formula $Al_2$-

$(OH)_{6-n}X_n$, wherein n has a value from about 0.80 to about 1.25 and X is selected from the group consisting of chlorine, bromine, iodine, sulfamate, sulfate, nitrate and mixtures thereof. The zirconium compound has the empirical formula $ZrO(OH)_{2-m}Y_m$, wherein m has a value of from about 0.50 to about 1.5 and Y is selected from the group consisting of chlorine, bromine, iodine and mixtures thereof. The third component is an amino acid which is a water soluble neutral amino acid, a most preferred amino acid being glycine and other suitable amino acids being alanine, beta-alanine, methionine, tryptophan, beta-phenylalanine, serine, valine and two-amino-butyric acid. The fourth component is an inorganic acid compound selected from the group consisting of aluminum chloride, hydrochloric acid and mixtures thereof. The complex should have an aluminum to zirconium molar ratio from about 2 to about 10, and the neutral amino acid should be present in the antiperspirant complex in such an amount that the molar ratio of neutral amino acid to total metal is from about 0.09 to about 0.24.

U.S. Pat. No. 2,814,584 discloses an antiperspirant composition including in combination an aqueous solution of a zirconium or hafnium salt of a strong monobasic mineral acid, a basic aluminum compound and urea. This patent discloses that while compounds of zirconium are relatively highly acidic and cannot therefore safely be used alone in contact with the skin, aqueous solutions of zirconium salts and hafnium salts, of strong monobasic mineral acids, may be rendered usable by treating them with certain basic aluminum compounds and urea, the basic aluminum compounds and the urea acting as buffering agents to bring the pH of the solution of the zirconium of hafnium salt to a value which renders it safe for antiperspirant usage. The zirconium and hafnium compounds which may be used, according to U.S. Pat. No. 2,814,584, are the chlorides, bromides, iodides and nitrates; the basic aluminum compounds which may be used have the general empirical formula $Al_2(OH)_{6-n}X_n$, where X is a monovalent acid anion of the group $Cl^-$, $Br^-$, $I^-$ and $NO_3^-$, and n has an average value from about 0.8 to about 2.

U.S. Pat. No. 2,814,585 discloses antiperspirant compositions including in combination an aqueous solution of a zirconium or hafnium salt of a strong monobasic mineral acid, a basic aluminum compound and an amino acid in which the number of amino groups is equal to the number of carboxyl groups in the molecule. The zirconium and hafnium compounds may be chlorides, bromides, iodides and nitrates. The basic aluminum compounds can have a general empirical formula $Al_2(OH)_{6-n}X_n$, where X is a monovalent acid anion of the group $Cl^-$, $Br^-$, $I^-$ and $NO_3^-$, and n has an average value from about 0.8 to about 2. This patent discloses that while the compounds of zirconium and hafnium are relatively highly acidic and cannot safely be used alone in contact with the skin, aqueous solutions of such zirconium and hafnium salts may be rendered usable by treating them with the basic aluminum compounds and amino acids, such compounds and acids acting as buffering agents to bring the pH of the solution of the zirconium or hafnium salt to a value which renders it safe for antiperspirant uses.

While each of U.S. Pat. No. 4,331,609, U.S. Pat. No. 2,814,584 and U.S. Pat. No. 2,814,585 describe antiperspirant compositions including at least a basic aluminum compound, which can be a basic aluminum nitrate, as well as a zirconium compound, these patents do not disclose use of basic aluminum and/or zirconium compounds of enhanced efficacy. In addition, these patents disclose generally the use of nitrates among other anions and do not describe any benefits or advantages achieved utilizing nitrates, specifically, as compared to, e.g., halides; in fact, these patents disclose that the nitrates therein are equivalent to, e.g., the chlorides. Moreover, these patents do not disclose use of other oxoanions (e.g., univalent oxoanions) as part of the basic aluminum and/or zirconium compound of the antiperspirant composition. Furthermore, U.S. Pat. No. 4,331,609 only discloses use of a basic zirconium halide, and does not teach use of basic zirconium compounds containing a univalent complex oxoanion such as nitrate. None of these U.S. patents achieve the objectives of the present invention.

U.S. Pat. No. 4,606,915 discloses a composition of a stannic halide and an aluminum halohydrate and also preferably containing a neutral amino acid, being useful in inhibiting perspiration when applied to the skin of a subject in powder form or when incorporated in a liquid or solid vehicle. In this patent, there is no disclosure that the aluminum has enhanced activity, nor that the resultant basic tin/aluminum halohydrate demonstrates enhanced antiperspirant activity. The contents of U.S. Pat. No. 4,606,915 are incorporated herein by reference in their entirety.

Accordingly, it is still desired to provide basic aluminum materials with enhanced antiperspirant activity; and compositions of (1) zirconium, hafnium, tin and/or titanium active antiperspirant material, either those conventionally known or those having enhanced antiperspirant activity, with (2) basic aluminum material having enhanced antiperspirant activity; which material and composition can be made without high temperatures and/or high pressures, and without the need for extra manufacturing steps of heating diluted solutions of already manufactured basic aluminum compounds. There is also still a need to provide basic aluminum antiperspirant materials with enhanced activity, and compositions containing the same, which can be provided in concentrated aqueous solutions, with improved compositional stability (that is, wherein the enhanced activity is not substantially reduced over a period of time).

SUMMARY OF THE INVENTION

Accordingly, it is an object of the present invention to provide a basic aluminum antiperspirant active material having enhanced antiperspirant activity, which can be produced at lower temperatures, at faster rates, and at higher initial solution aluminum concentrations; particularly at lower temperatures, higher initial solution aluminum concentrations and faster rates than those utilized for producing basic aluminum halide active antiperspirant material having enhanced efficacy, and methods of forming such material.

It is another object of the present invention to provide a basic aluminum antiperspirant active material with enhanced activity, and methods of forming such material, wherein the material can be provided without the need for the extra manufacturing step of heating diluted solutions of already manufactured basic aluminum materials at high temperature or high pressure conditions.

It is a further object of the present invention to provide a basic aluminum antiperspirant material having enhanced efficacy, which has improved stability in aqueous solution (that is, retains its enhanced activity, as shown by increased peak 4 relative area) over extended periods of time, and methods of producing such material.

It is an additional object of the present invention to provide an antiperspirant composition having enhanced antiperspirant efficacy, including a basic aluminum antiperspirant material having enhanced activity and a zirconium, hafnium, tin and/or titanium antiperspirant active material, which composition has improved stability in aqueous solution (that is, whose enhanced activity is not substantially reduced over a period of time), and which can be produced at lower temperatures, and methods of producing such composition.

The present invention achieves each of the above objects with a basic aluminum material (a polymeric aluminum material) having the empirical formula:

where $0.5 \leq a \leq 5.0$, X is an anion as described further infra, and wherein the antiperspirant active material is further characterized by:

(a) size exclusion high performance liquid chromatography peaks corresponding to peak 3 and peak 4 of the size exclusion chromatogram produced from a high performance liquid chromatography (HPLC) technique, discussed further infra;

(b) a peak 4 relative area of at least 25%, a peak 3 relative area of less than 60%, the sum of the relative peak 3 and peak 4 areas being at least 50%; and (c) less than 10% chromatographic peaks eluting at shorter retention times (or larger molecular sizes) than peak 3, corresponding to peaks 1 and 2.

As an illustrative example, the basic aluminum material according to the present invention can have a peak 4 relative area of at least 40% and a peak 3 relative area of less than 50%, all other characteristics of the basic aluminum material being as set forth in the preceding paragraph.

The anions (X) of the above-stated empirical formula, within the scope of the present invention, are univalent complex oxoanions of nitrogen, chlorine and other halogens, including, but not limited to, $NO_3^-$, $ClO_3^-$, $ClO_4^-$, and $IO_4^-$, which form salts with $Al^{3+}$ in aqueous solution, so that these salts are essentially completely dissociated, which anions are readily soluble in water with metallic ions in the solution (for example, Al ions; or, where the solution contains other antiperspirant active materials such as Zr, Hf, Ti and/or Sn antiperspirant active materials, Al ions and the metallic ions of the other antiperspirant active materials), and which form conjugate acids that are strong acids. By strong acid, we mean those acids having the ability to substantially completely dissociate $H^+$ (e.g., at least 98% dissociated) in aqueous solution. Furthermore, those anions within the scope of the present invention are labile with respect to undergoing reduction, the products of said reduction being gases or soluble anions of lower oxidation states of nitrogen or halogen than in the starting anion (the starting anion is the anion of the Al salt used to form the basic aluminum material of the present invention, as discussed further infra). A preferred anion is the nitrate anion ($NO_3^-$).

Various anions which can be utilized as part of the present invention have been set forth above, as well as functional characteristics of usable anions in general. Sulfate and phosphate anions (and similar anions) will not work as part of the present invention, because they complex to too great an extent with aluminum.

Preferably, "a" of the above-described empirical formula is greater than or equal to 0.9 and less than or equal to 2.5. More preferred is materials of the above-referred-to empirical formula wherein "a" is greater than or equal to 0.9 and less than or equal to 1.9.

Preferred relative areas for peak 3 and peak 4 of the polymeric material is a peak 4 area of at least 35%, but less than 80%, and a peak 3 area of less than 50%, the sum of the peak 3 and peak 4 areas being at least 60% and less than 90%, with essentially no peaks 1 and 2.

Other preferred relative areas for peaks 3 and 4 include a peak 4 area of at least 40%, but less than 70%, and a peak 3 area of less than 40%, the sum of the peak 3 and peak 4 areas being at least 70% and less than 95%, with essentially no peaks 1 and 2.

Particularly when the nitrate anion is used as part of the present invention, the peak 4 relative area is increased (thereby showing increased enhanced activity of the basic aluminum material). Specifically, when utilizing nitrate anion as part of the basic aluminum material, the favored polymer size is that shown under peak 4 of the size exclusion chromatogram. In the present invention, utilizing, for example, the nitrate anion, upon addition of metallic aluminum to a solution of aluminum nitrate nonahydrate as described further, infra, the polymeric aluminum complex species comprising peak 4 are formed very rapidly with only small quantities of larger molecular weight peaks such as peaks 3, 2 or 1. In comparison, in forming conventional, non-enhanced active aluminum halohydrates, a significant amount of peak 3 is formed simultaneously with peak 4; and this peak 3, and earlier, larger molecular weight peaks rapidly become larger in area than peak 4 and eventually dominate the HPLC chromatogram. Therefore, in order to form enhanced activity aluminum halohydrates, dilution and heating of manufactured active material are necessary to form the desired levels of peak 4 (that is, to depolymerize larger molecular weight aluminum complex species, such as represented by peaks 2 and 3, into smaller species represented by peak 4). Furthermore, when enhanced aluminum halohydrates are formed directly from addition of metallic aluminum to a solution of aluminum halide without the extra dilution and heating step mentioned above, the initial aluminum halide concentration of the solution must be maintained at relatively low levels. Such diluted initial solutions are unnecessary according to the present invention. Thus, when forming the enhanced activity aluminum material according to the present invention, the material can be formed more quickly, at lower temperatures, at higher initial solution aluminum concentrations, and will have more peak 4 material, as compared to the corresponding halide. The basic aluminum material of the present invention has substantially no species with a size greater than 100 Å.

Furthermore, the pH of the basic aluminum materials within the scope of the present invention is higher than the corresponding basic aluminum halide materials; thus, the materials within the scope of the present invention are gentler on the skin of axillary areas, as compared to the corresponding basic aluminum halide materials.

The above objects are further achieved according to the present invention by providing a basic antiperspirant material having enhanced efficacy, wherein the basic aluminum material contains at least 25% by weight of the aluminum in the form of Al$^b$. This material can be produced without the need for low temperature conditions, without the need for shorter reaction times, or reactive forms of aluminum metal or catalysts, without the need for low initial aluminum concentrations in solution, and without the need for aging previously manufactured basic aluminum antiperspirant materials.

The basic aluminum materials of the present invention can be produced at relatively low temperatures, substantially lower than 90° C. (for example, at temperatures below 45° C.). Generally, temperatures from below 45° C., up to 140° C., can be utilized for forming the basic aluminum material with enhanced antiperspirant activity of the present invention, the preferred temperature range being 45° C.-100° C., and particularly less than 90° C. The time of heating, in the temperature range of 45° C.-140° C., can be 0.5-17 hours. Solutions of 1.0 molar aluminum (37.5% by weight aluminum nitrate nonahydrate) and higher can be utilized for forming the basic aluminum material of the present invention. Thus, as seen herein, the processing for forming the basic aluminum materials of the present invention is at lower temperatures, and/or for smaller amounts of time, and at higher initial aluminum solution concentrations, than with techniques for forming conventional basic aluminum materials having enhanced antiperspirant activity.

The concentration of the monomeric aluminum compound in aqueous solution, used in forming the basic aluminum material of the present invention, is not critical, and can be modified depending on temperature and pressure conditions of the formation. For example, an initial solution of 28% by weight Al(NO$_3$)$_3$.9H$_2$O, which is heated to provide the material of the present invention, can be used. While not limiting, the beginning solution can include 19%-38% by weight of the aluminum compound (for example, Al(NO$_3$)$_3$.9H$_2$O), but such starting concentration can be lower than 19% or can go up to 40%-45% with changes in temperature and/or pressure.

The method of forming the basic aluminum material of the present invention involves dissolving the aluminum salt of the aforementioned univalent oxoanions in water, heating, and (while heating) adding additional aluminum in the metallic form. In general, the reaction could be written as follows:

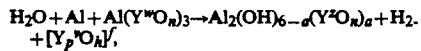

$$H_2O + Al + Al(Y^wO_n)_3 \rightarrow Al_2(OH)_{6-a}(Y^zO_n)_a + H_2 + [Y_p^rO_h]^f,$$

where a is as defined previously, Y$^z$O$_n$ is a univalent oxoanion of nitrogen or halogen described previously as X, p is 1 or 2, $0 \leq h \leq 5$, w is the oxidation state of nitrogen or halogen, n is dependent upon the oxidation state of Y, f is 0 or $-1$, $0 \leq v < w$, and $0 < z \leq w$. The relationship between w and v represents an overall reduction of the Y atom resulting in a lower oxidation state for that atom in the Y$_p^r$O$_h$ by-product than in the original Al(Y$^w$O$_n$)$_3$. As is clear from the foregoing reaction scheme, the anion of the aluminum salt reactant is labile with respect to undergoing reduction. Moreover, as indicated previously, the product of the reduction (Y$_p^r$O$_h$) is a gas or soluble substance.

For a=1 and Y$^z$O$_n$=NO$_3$ in the above equation, the following reaction scheme is one of several non-limiting ways to represent the method of the present invention;

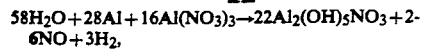

$$58H_2O + 28Al + 16Al(NO_3)_3 \rightarrow 22Al_2(OH)_5NO_3 + 26NO + 3H_2,$$

where the production of nitric oxide represents a reduction of the nitrate oxoanion from a formal +7 to +2 oxidation state on the nitrogen atom.

In the foregoing description concerning the method of forming the basic aluminum material, it is described that the aluminum salt of the univalent oxoanion (Al(Y$^w$O$_n$)$_3$) is dissolved in water, with additional aluminum being added (while heating). However, the formation of the basic aluminum material of the present invention can be practiced by preparation of the aluminum salt of the univalent oxoanion in situ, by mixing aluminum metal with an inorganic acid, HY$^w$O$_n$, where H represents H$^+$, permitting the aluminum metal to dissolve (heating is usually necessary, typically between 45°-140° C.); and then continuing the reaction by addition of more aluminum metal to the formed Al(Y$^w$O$_n$)$_3$ according to the above description. The acid utilized in the in situ formation of Al(Y$^w$O$_n$)$_3$ can be, illustratively (but not limitingly) HNO$_3$, HClO$_4$, HClO$_3$, and HIO$_4$. In forming the nitrate, HNO$_3$ is used.

In the direct preparation of the present invention, antiperspirant active material containing a high peak 4 relative area also contains a substantial proportion of this peak 4 material in the form of polymers which complex with the ferron (8-hydroxy-7-iodo-5-quinoline sulfonic acid) ligand at a reaction rate which is characteristic of polyhydroxyaquoaluminum species referred to in the art as Al$^b$. In one embodiment of the present invention, at least 25% by weight of the aluminum of the basic aluminum antiperspirant active material is in the form of Al$^b$ polyhydroxyaquoaluminum species. Typically, the anti-perspirant active material of this invention contains up to 50% by weight of the total aluminum in the form of Al$^b$. In the art, polyhydroxyaquoaluminum species have been shown to be made up of three broad groups by spectrophotometrically following their complexing rates with this ferron reagent. Such groups have been referred to as Al$^a$, Al$^b$ and Al$^c$. The first group, Al$^a$, has the fastest complexing rate (almost instantaneous); the Al$^b$ group has an intermediate complexing rate (the reaction is complete in an hourly time range); and the Al$^c$ group has the slowest rate (generally the reaction requires several days for completion). It is known that when basic aluminum materials utilized as antiperspirants are subjected to size exclusion high performance liquid chromatography, the three groups exhibit different retention times. The Al$^a$ group has the longest retention times which is indicative that it is made up of the lowest molecular size materials; the Al$^b$ group exhibits intermediate retention times, indicating that it comprises polymeric species of intermediate molecular sizes; and the Al$^c$ group has the shortest retention times, indicating that it is made up of the highest molecular size polymeric species.

U.K. Patent Application No. 2,048,229 describes a group of complexes (Al$^{c'}$) within the aluminum chlorhydroxides which is more efficacious as an antiperspirant, and which complexes with a ferron reagent at a reaction rate characteristic of Al$^c$. This U.K. Patent Application No. 2,048,229 describes a method of aging presently available (commercial) basic aluminum chloride in order to obtain the Al$^{c'}$ group of complexes. This U.K. Patent Application No. 2,048,229 does not disclose the desire to obtain, nor the evidence of, increased Al$^b$ concentrations.

The present invention also includes incorporating the basic aluminum antiperspirant material with enhanced antiperspirant activity, as described above, as part of the following composition:

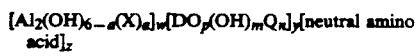

where a and X are as defined previously, w:y ranges from about 0.3:1 to about 6.0:1, z:y ranges from 0 to 1.3:1 and p is either 0.0 or 1.0. When p=0, then m=0 and n=4; when p=1, then m+n=2. D is a metal cation selected from Zr, Hf, Ti or Sn and Q is a halide, such as Cl, $NO_3$, or any of the univalent oxoanions further described herein. Generally, the metal cation compound selected from Zr, Hf, Ti or Sn includes those known as active antiperspirant materials, and which are compatible with the basic aluminum material of the present invention. The preferred neutral amino acid is glycine but may be alanine, phenylalanine or other known neutral amino acids. Within the above-referred-to range for w:y, this ratio can be from about 0.3:1 to about 2.0:1.

Such composition is further characterized by size exclusion high performance liquid chromatography peaks corresponding to peak 3 and peak 4 of the standard basic aluminum/zirconium polymer solution HPLC size exclusion chromatogram, with a peak 4 relative area of at least 25% and a peak 3 relative area of less than 50% (e.g., less than 15%). Unlike the basic aluminum antiperspirant material, the active composition of the present invention, containing a zirconium compound component, for example, may contain significantly more than 10% chromatographic peaks eluting at shorter retention times than peak 3, corresponding to peak 1 and not peak 2, said composition having less than 10% chromatographic peaks corresponding to peak 2. For example, the zirconium compound component could contribute more than 10% peak 1 to the active composition. The active composition of the present invention may contain up to 35% chromatographic peak 1 corresponding to the zirconium compound component of the composition.

The composition can be prepared by simple mixing of a solution of the basic aluminum material having enhanced antiperspirant activity, provided by mixing a solution of a basic aluminum compound as discussed above, with a solution of the Zr, Hf, Ti and/or Sn material (for example, a solution of zirconyl hydroxychloride compound). The temperature of such mixing can be at least room temperature, for example, at room temperature. Such mixing need not be at room temperature, and can be (illustratively, but not limiting) at 45°–140° C., preferably 45°–100° C., even more preferably 45°–90° C., corresponding to temperatures for forming the basic aluminum material according to the present invention.

The composition of the present invention can easily be provided, without dilution and/or heating. Specifically, since the present composition can be provided without heating, the composition is much more stable in water, as compared to corresponding compositions utilizing aluminum chlorhydrate of enhanced antiperspirant activity. Of course, if the mixing of (1) Zr, Hf, Ti and/or Sn material and (2) aluminum material were performed with dilution and/or heating, an even more efficacious composition could be provided.

The basic aluminum antiperspirant material of the present invention, or the composition of the present invention including the basic aluminum material, can be obtained in powdered form from an aqueous solution by spray-drying or freeze-drying, for example. The conversion of the aqueous antiperspirant solution to a dried (for example, spray-dried) antiperspirant powder can be accomplished by any one of many techniques known to those skilled in the art, and these techniques are more or less suitable for commercial use.

Accordingly, the present invention achieves an antiperspirant active material, and composition containing such active material, which can be produced under relatively low temperature and/or low pressure conditions, and in relatively concentrated solutions, whereby production costs can be reduced. Moreover, the present invention achieves an antiperspirant material, and composition containing such material, which maintains enhanced activity over a relatively long period of time (that is, has a stable enhanced activity).

BRIEF DESCRIPTION OF THE DRAWINGS

FIGS. 22–24 are high performance liquid chromatography size exclusion chromatograms of compositions according to the present invention, formed in various of the examples.

DETAILED DESCRIPTION OF THE INVENTION

Figure 1:
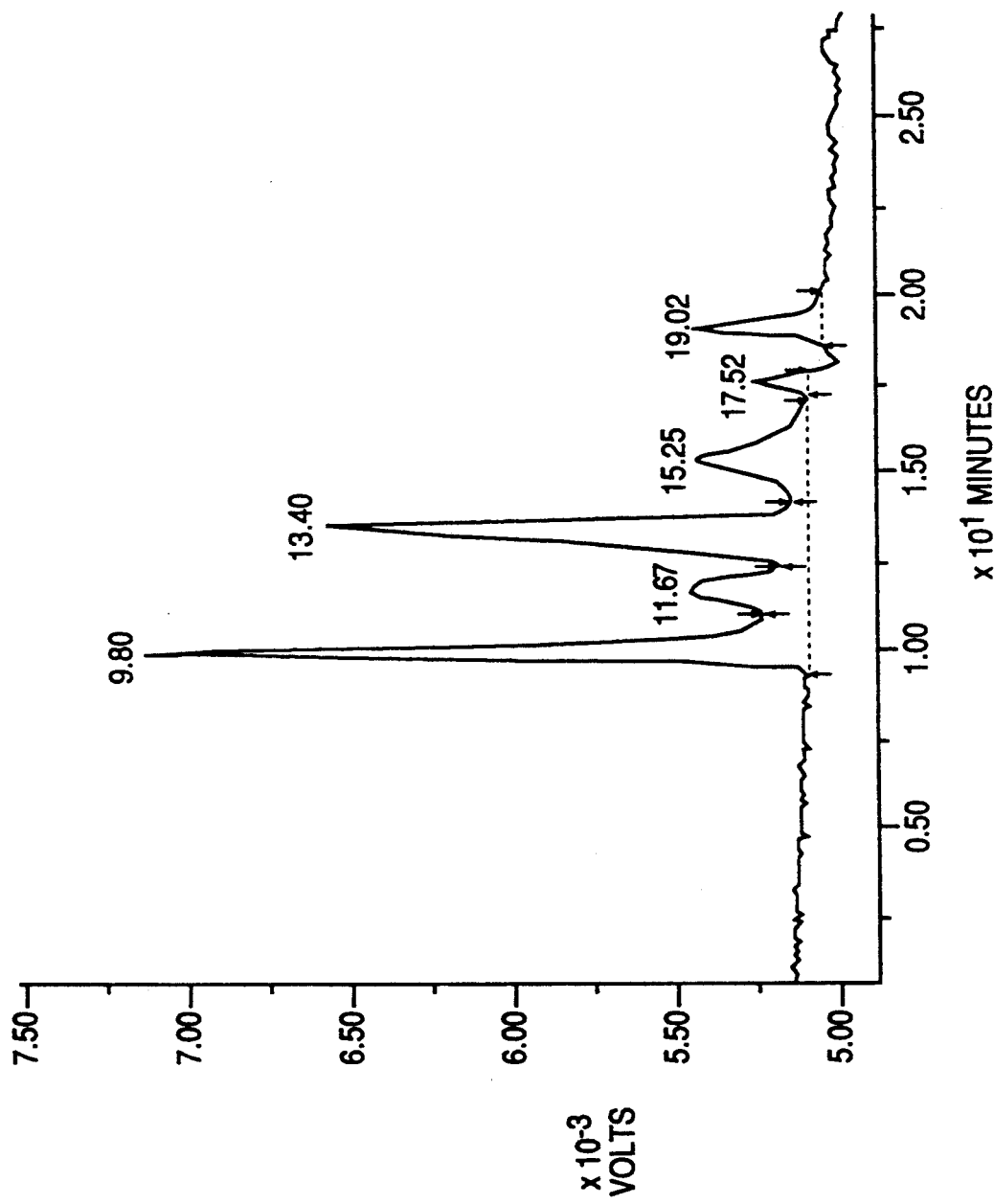
FIG. 1 shows a high performance liquid chromatography size exclusion chromatogram for a composition of zirconyl hydroxychloride and aluminum nitratohydrate within the scope of the present invention.

While the invention will be described in connection with specific and preferred embodiments, it will be understood it is not intended to limit the invention to those embodiments. On the contrary, it is intended to cover all alterations, modifications and equivalents as may be included within the spirit and scope of the invention as defined by the appended claims.

Prior to the detailed description of the present invention, the analytical chromatographic and ferron complexation procedures for determining the peak 4 and peak 3, and $Al^a$, $Al^b$ and $Al^c$, values in connection with the present invention will be set forth in the following.

The analytical chromatographic procedure is performed using pre-packed Bondagel silica-based columns available from Waters Associates in 3.9 mm (ID) by 30 cm steel columns. A combination of Bondagel E-125 and/or Porosil GPC 60 A° columns connected in series is used. The column mobile phase is 0.01M nitric acid. The mobile phase is pumped through the columns at a 0.5 ml/minute flow rate using a high performance liquid chromatography pump system (e.g., Waters model 501 or 510). A refractive index detector (e.g., Waters model 401 or 410) is used to detect sample fractions as they are eluted from the columns. The detector is linked to a printer or plotter to provide a chromatogram and to an integrator which measures the elution times or volumes of the fractions and the relative chromatographic peak areas. The Waters model 730 Data Module is an example of a printer, plotter integrator. Many computerized systems are also available. Microliter quantities of the aqueous antiperspirant solutions of interest are injected into the column system with a micro-syringe using an injector system such as the Waters model U6K.

Those skilled in the art will obtain size exclusion high performance liquid chromatograms which resemble those provided in the figures by judicious selection of column types, length of columns, flow rates, recorder-/integrator type and sensitivity, detector type and sensitivity. Furthermore, those skilled in the art will be able to make peak assignments, relative to appropriate standards, so that peak 3 and peak 4 will be easily distinguishable from other peaks of shorter and longer relative retention times.

To elaborate, peak 3 and peak 4 always elute in sequential order, that is, peak 3 is prior to and distinguishable from the subsequent peak 4 (peak 3 elutes at shorter retention times than peak 4). These peaks fall within a HPLC peak series which elute in order of decreasing apparent molecular volume. The earliest peak, designated as peak 1, representing the highest molecular volume, does not contain aluminum and may only be present in polymeric species of the antiperspirant composition and not the antiperspirant material of the present invention. Peaks 2–8 are present in both mixed metal systems (e.g., aluminum/zirconium) and in non-mixed metal systems containing only aluminum. Peak 8 is due to the totally included species (limit of column interstitial volume) most likely due to inorganic acid. Relative retention times have been calculated for each of the chromatographic peaks as the ratio of their retention times to the retention time of this totally included group of molecular species. Average values of 0.61 for peak 3 (0.59–0.64) and 0.69 for peak 4 (0.64–0.75) have been found. The exact retention times (or relative retention times) of each peak can be reproduced accurately. However, comparison to a standard basic aluminum polymer solution HPLC size exclusion chromatogram alleviates any problems caused by flow rate deviations, column bed degradation or sample preparation adjustments (concentration, injection volume, etc.).

Peak areas as reported are calculated by a chromatographic algorithm which integrates the area under each peak from its start to finish as the peak boundaries touch a horizontal baseline as a reference point. If resolution of two adjacent peaks is inadequate, a perpendicular line from the lowest point of the valley between them is dropped to the horizontal baseline to designate the endpoint of the prior peak and the starting point of the subsequent peak. These areas are then mathematically totalled and the percentage of each peak area relative to the total chromatographic peak areas is reported.

The reaction is monitored by removing aliquots of reaction medium every 0.5 hour. The heating is discontinued once the HPLC profile corresponds to the previously mentioned peak parameters. This is followed by filtering off the excess aluminum, and, if a solid or powder form is desired, by spray-drying of the solution.

The ferron complexation reaction procedure is performed by following the reaction of the ferron reagent (L) with the polyhydroxyaquoaluminum species. The absorbance at 368 nm of the aluminum ion-ferron reagent complex ($AlL_3$) was monitored over time relative to that of the free ligand (L). The ligand solution was prepared by the addition of 5 ml of a $5.7 \times 10^{-3}$ molar ferron solution, 2 milliliters of a 1.4 molar hydroxylamine hydrochloride/0.48 molar hydrochloric acid solution, and 2 milliliters of a 2.6 molar sodium acetate solution to 25 milliliters of deionized water. The amine/weak acid salt combination buffers the solution at pH 5. To this, 2 milliliters of a 0.02% (w/w) aluminum sample (approximately $1.5 \times 10^{-3}$ molar Al) is added and the absorbance of the analyte solution is recorded within three minutes and every 30 minutes thereafter up to 6 hours. Daily readings were taken up to 10 days. The absorbance due to the $AlL_3$ complex was determined at each time period and sequential absorbance differences between absorbance values at 3 minutes, 6 hours and 10 days provided the $Al^a$ (low molecular weight), $Al^b$ (intermediate oligomeric size) and $Al^c$ (larger polymeric species) distribution in aqueous solution.

The present invention contemplates a basic aluminum material (that is, a polymeric aluminum compound) having the empirical formula $Al_2(OH)_{6-a}(X)_a$, where $0.5 \leq a \leq 5.0$, and where X is a univalent complex oxoanion of nitrogen, chlorine and other halogens having specified characteristics, characterized by (a) size exclusion high performance liquid chromatography peaks corresponding to peak 3 and peak 4 of the size exclusion chromatogram produced from high performance liquid chromatography; (b) a peak 4 relative area of at least 25% (illustratively, at least 40%), a peak 3 relative area of less than 50%, the sum of the relative peak 3 and peak 4 areas being at least 50%; and (c) less than 10% chromatographic peaks eluting at shorter retention times (or larger molecular sizes) than peak 3, corresponding to peaks 1 and 2. Most preferably, X of the above-described formula is the nitrate anion.

Moreover, the present invention contemplates a method of forming such basic aluminum material, wherein the material can be formed at relatively high initial aluminum solution concentrations, low temperatures and/or relatively low pressures; however, the material can also be formed at high temperatures and high pressures, and at low initial aluminum solution concentrations.

In addition, the present invention contemplates an antiperspirant composition including such above-described basic aluminum material, a zirconium, hafnium, tin and/or titanium antiperspirant active material (such as zirconyl hydroxychloride) and an optional neutral amino acid, and a method of forming such composition.

According to the present invention, basic aluminum materials, or basic aluminum/zirconium, hafnium, tin and/or titanium materials, with enhanced antiperspirant activity can be provided without the need of using high temperatures or low initial aluminum solution concentrations, special forms of aluminum metal, catalysts and without the need for extra manufacturing steps of heating diluted solutions of already manufactured basic aluminum or basic aluminum/zirconium, hafnium, tin and/or titanium compounds at high temperature or high pressure conditions or for long periods of time, thus reducing the time and cost of manufacturing. Relatively concentrated solutions of the present invention show improved compositional stability; that is, the areas of peak 4 and peak 3 of the high performance liquid chromatography size exclusion chromatogram remain stable for long time periods at solution concentrations of 15 to 25 wt. %.

Specifically, the basic aluminum material of the present invention can be prepared at temperatures substantially lower than 90° C. As a non-limiting, specific example, 46.6 grams of aluminum nitrate nonahydrate is dissolved in deionized water to give 248.6 grams of total solution. The solution is heated to 45° C., and 33.52 grams of aluminum (small turnings of aluminum, that is, approximately 1/16" to 1/8" long oblong pieces, 1/100' to 3/100" thick), added in excess, is added over a two minute period. While small turnings of aluminum were added in the present non-limiting example, aluminum can be added in the form of powder, pebbles, ingots, etc. Heating at 45° C. continued with continuous stirring for a total of 17 hours. Aliquots of the resulting supernatent solution (which is filtered to remove excess aluminum) are found to exhibit a relative high performance liquid chromatography size exclusion peak 4 area of 65% and a peak 3 area of 9%. These area percents compare to 5-15% peak 4 and 40-55% peak 3 found in commercial preparations of aluminum chlorhydrate, and the 30-45% peak 4 and 40-50% peak 3 found in current art enhanced active aluminum chlorhydrates.

In the following will be described non-limiting, specific examples for forming an aluminum/zirconium composition according to the present invention. Thus, 21.7 grams of aluminum nitratohydrate prepared according to the present invention (that is, a basic aluminum material within the scope of the present invention), containing approximately 18.9% by weight aluminum nitratohydrate in solution, is mixed with 6.18 grams of a 25.8% by weight solution of ZrO(OH)Cl, 0.50 grams of solid glycine and 1.25 grams of water with stirring, to form a composition of aluminum/zirconium according to the present invention.

As a second example, prepared as in the first example, 23.47 grams of the aluminum nitratohydrate solution, 12.36 grams of the ZrO(OH)Cl solution, 1.0 grams of solid glycine and 19.4 grams of water were mixed at room temperature.

FIG. 1 shows the size exclusion chromatogram for an aluminum nitratohydrate/zirconyl hydroxychloride/glycine composition according to the present invention (the foregoing first example). As can be seen in this FIG. 1, the relative area of peak 4 is 34.2% and the relative area of peak 3 is 10.7%.

As indicated previously, the antiperspirant compound can be obtained in powdered form from the above-described aqueous solutions by drying (for example, spray-drying or freeze-drying). In the following will be described a non-limiting example for spray-drying the aqueous solutions. Thus, for such spray-drying, a Buchi 190 Mini Spray Dryer is used with an inlet temperature ranging from 200° C.-230° C., and with an outlet temperature ranging from 85° C.-110° C. Two to three hours are required to spray-dry 1,200 grams of liquid solution containing the antiperspirant compound. In the spray-drying process, the spray-dryer unit is heated to the desired inlet temperature. As soon as the inlet temperature has stabilized, the outlet temperature is adjusted and stabilized with distilled water; this is achieved by varying the output of the pump. When the desired values have been achieved, the unit is ready for spray-drying the antiperspirant solution. Depending on the concentration of the solution, the outlet temperature will rise more or less and should be adjusted accordingly.

While a specific spray-drying technique has been disclosed, the conversion of the aqueous antiperspirant solution to a dried antiperspirant powder can be accomplished by any one of many techniques known to those skilled in the art, these methods being more or less suitable for commercial use. Accordingly, such specific spray-drying technique as described above is not a limitation on the present invention.

The material and composition of the present invention can be incorporated as a substitute for the active antiperspirant substance in various conventional antiperspirant forms for axillary application, such as aqueous and alcoholic solutions, solid sticks, roll-ons (suspensions of dried active material, lotions, solutions, water-in-oil emulsions or oil-in-water emulsions), gels, creams, pressed powders, aerosols, etc. U.S. Pat. Nos. 4,359,456, 4,606,915 and British Patent Specification No. 1,568,831, the contents of each of which have already been incorporated herein by reference, are noted for their disclosures of various antiperspirant components, with which the material and composition of the present invention can be blended for forming antiperspirants for axillary application. The material and composition of the present invention is used in the antiperspirants in amounts equal to and greater than the amounts of conventional enhanced activity antiperspirant materials used in antiperspirants. For example, any emulsion (water-in-oil or oil-in-water) antiperspirant roll-on product can be prepared with 10-25% by weight of the material and composition of the present invention without concern for the loss of enhanced antiperspirant activity.

Various specific examples of the present invention are set forth in the following. Of course, such examples are illustrative and are not limiting. In connection with the following examples are provided size exclusion chromatograms for products formed in such examples. Such chromatograms were obtained utilizing the analytical chromatographic procedure discussed previously. In the following examples, the ferron results are on a weight % basis of the basic aluminum material.

EXAMPLE 1

Figure 2:
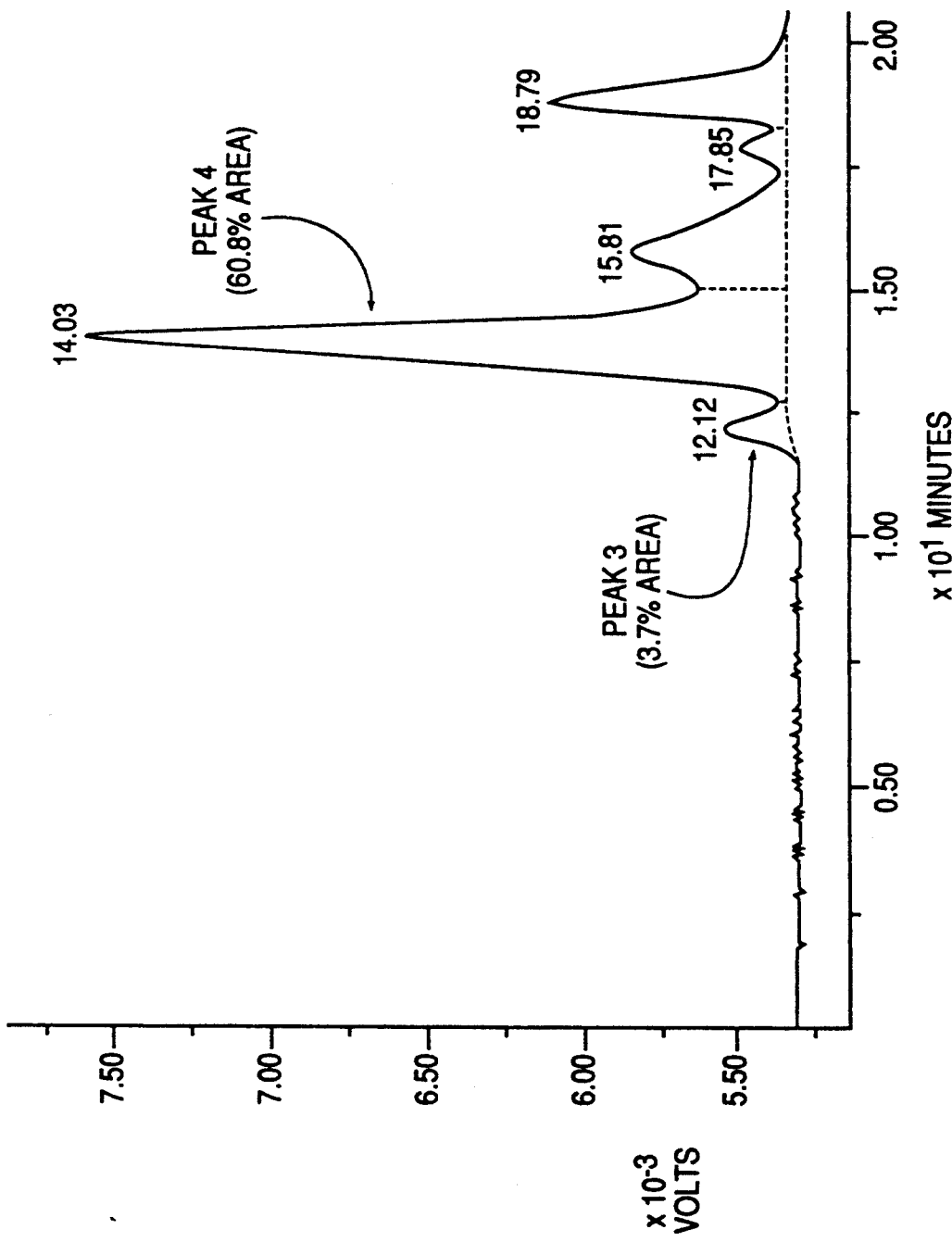
FIGS. 2–21 are high performance liquid chromatography size exclusion chromatograms of basic aluminum materials formed in the various examples.
Figure 3:
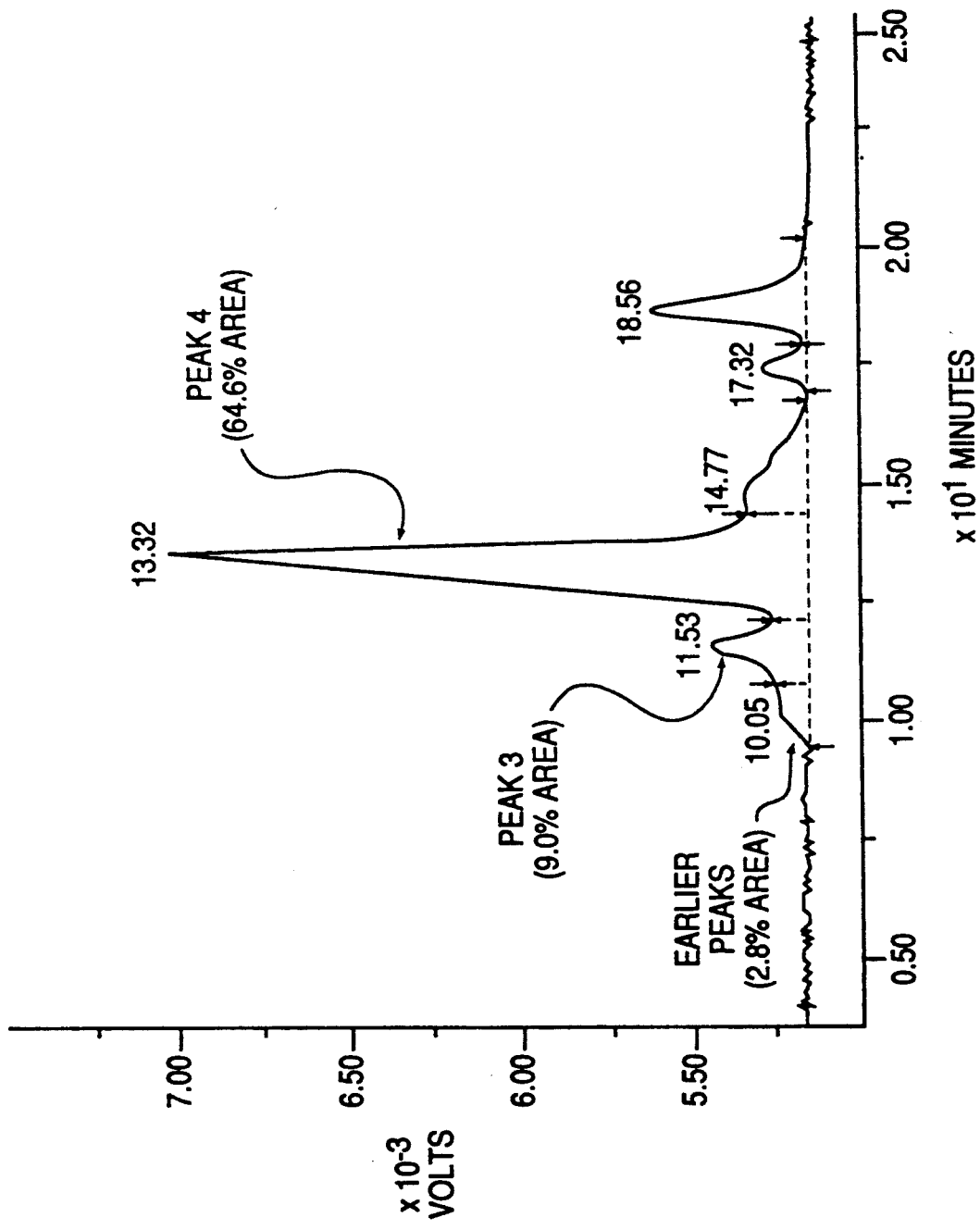

46.6 grams of aluminum nitrate nonahydrate are dissolved in deionized water to give 248.6 grams of total solution. The resultant 0.5M solution is warmed to 37° C. over a two-hour period. 33.52 grams of aluminum metal (small turnings) are added over two minutes. The reaction temperature is raised to 45° C. over a two hour period and this temperature is maintained at 45° C.-50° C. with continuous stirring for a total of seventeen hours from aluminum metal addition. Aliquots of the resulting supernatent solution are found to exhibit a relative HPLC (high performance liquid chromatography) size exclusion chromatographic peak 4 area of about 61% and a peak 3 area of 3.7%, as seen in FIG. 2. The reaction mixture was allowed to cool to room temperature by removing the heating mantle, and was kept at room temperature for an additional six and one-half hours. The chromatographic profile of the supernatent solution does not change significantly during this six and one-half hour period; however, the reaction does continue during this period, so that aliquots of the supernatent solution exhibit a peak 4 area of about 65% and a peak 3 area of 10% after seventeen hours at 45° C.-50° C. and six and one-half hours at room temperature. The reaction mixture is then reheated to 45° C. over a thirty minute period and the temperature is maintained at 45° C.-50° C. for another seven hours with continuous stirring. The reaction mixture is filtered to remove unreacted aluminum, and the resultant solution after twenty-four hours at 45° C.-50° C. exhibits a pH of 4.4 and contains 65% peak 4 area, 9% peak 3 area, and a small amount (roughly 3%) of earlier peaks 1 and 2, as seen in FIG. 3. A total of 6.53 grams of aluminum reacted.

EXAMPLE 2

Figure 4:
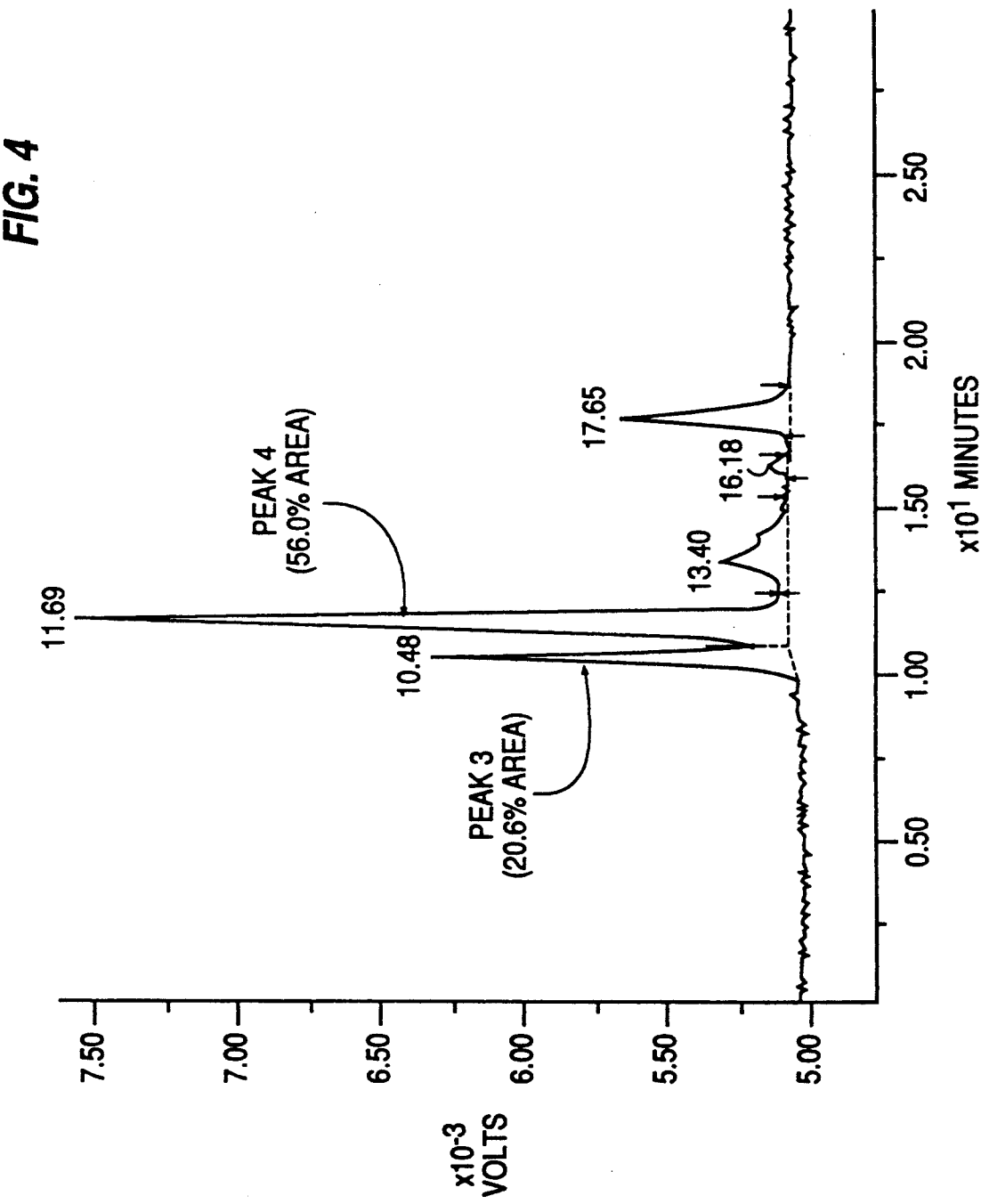

69.9 grams of aluminum nitrate nonahydrate are dissolved in deionized water to give 248.4 grams of total solution. The resultant 0.75M solution is heated to 68° C. over a thirty minute period. 50.18 grams of aluminum metal (small turnings) are added over two minutes. The reaction temperature is raised to 85° C. over a one and one-half hour period, and a temperature of 78° C.–80° C. is then maintained with continuous stirring for another eighty minutes. After a total of two hours and fifty minutes from the addition of aluminum metal, the reaction mixture is filtered to remove unreacted aluminum. The resultant solution exhibits a pH of 3.75 and contains 57% peak 4 area, 17% peak 3 area, and no earlier chromatographic peaks. A total of 8.72 grams of aluminum reacted. The solution is spray-dried using the spray-drying technique described earlier. Analytical analysis of spray-dried powder indicates that it contains 19.72% aluminum and 5.74% nitrogen. A 15% solution of this spray-dried powder in deionized water is found to exhibit a pH of 4.15 and contains 56% peak 4 area and about 21% peak 3 area, as shown in FIG. 4. The ferron reaction results in 21.1% $Al^a$, 36.7% $Al^b$ and 42.2% $Al^c$.

EXAMPLE 3

Figure 5:
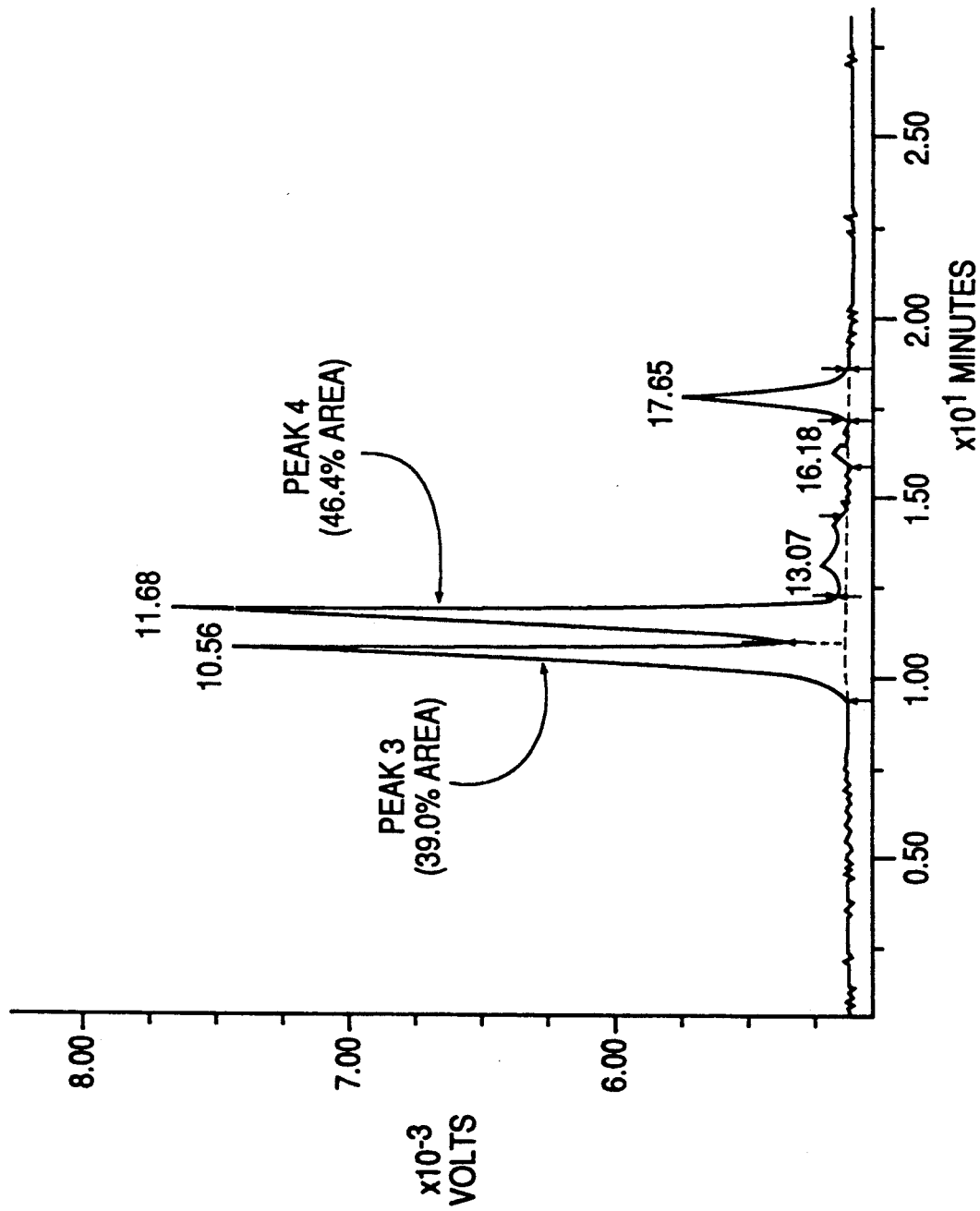

93.2 grams of aluminum nitrate nonahydrate are dissolved in deionized water to give 248.4 grams of total solution. The resultant 1.0M solution is heated to 67° C. and 67.04 grams of aluminum metal (small turnings) are added. The reaction temperature is maintained at 79° C.–90° C. for a total of two hours and forty-five minutes following the addition of the aluminum metal, with continuous stirring. The reaction mixture is filtered to remove unreacted aluminum metal and immediately spray-dried using the spray-drying techniques described earlier. The resultant powder was dissolved in deionized water to make a 15% solution and was found to exhibit a pH of 4.30, and contained about 46% peak 4 area and 39% peak 3 area, as seen in FIG. 5. A total of 11.68 grams of aluminum metal reacted. The ferron reaction results in 6.2% $Al^a$, 34.2% $Al^b$ and 59.6% $Al^c$.

EXAMPLE 4

Figure 6:
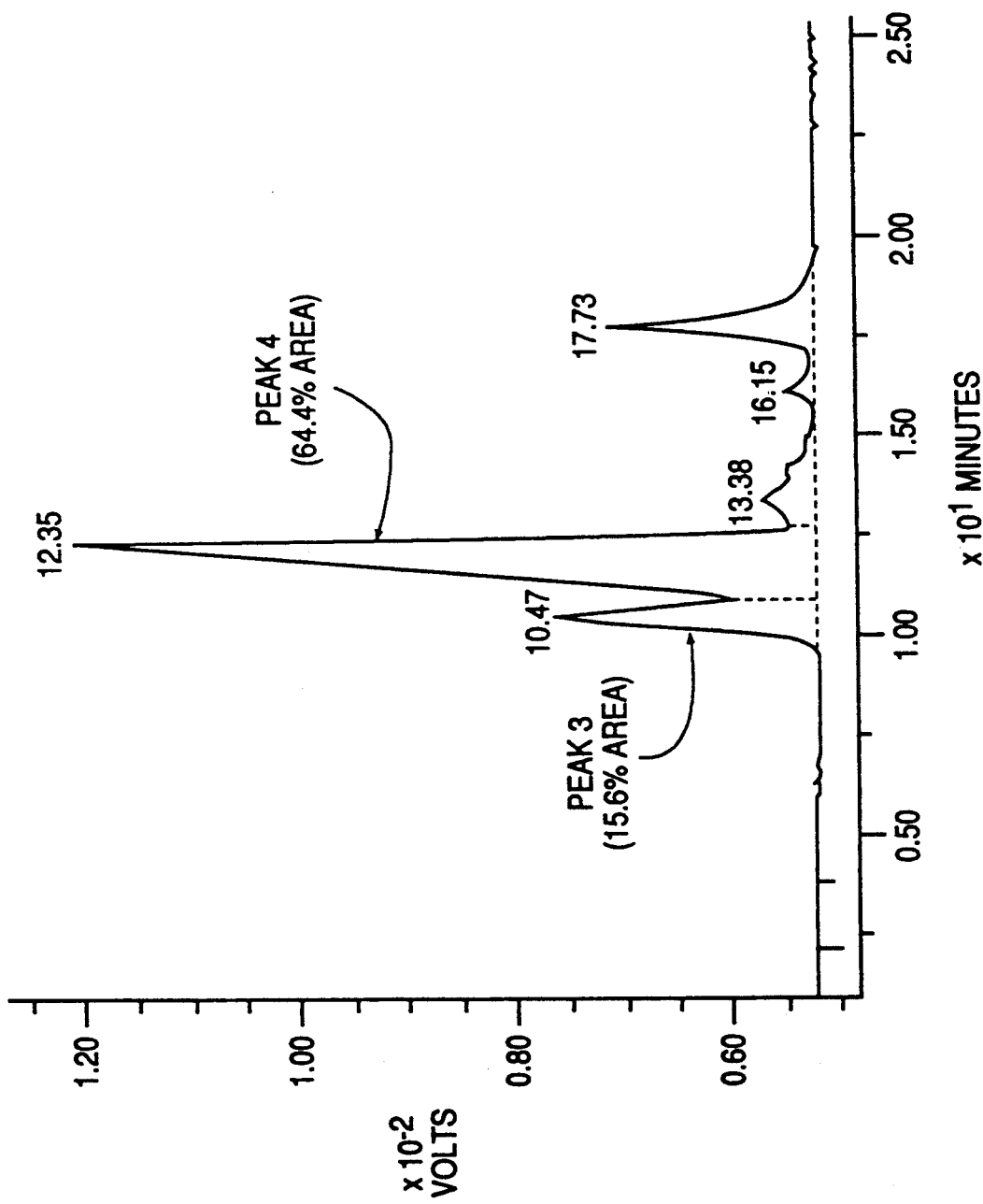

349.5 grams of aluminum nitrate nonahydrate are dissolved in deionized water to give 1,242 grams of total solution. The resultant 0.75M solution is heated to 65° C., and 250.9 grams of aluminum metal (small turnings) are added over a five minute period. The reaction temperature rises to 97° C. during the aluminum metal addition, and is then cooled with an ice bath or heated with a heating mantle to maintain a temperature between 62° C. and 87° C. for a total of three hours following aluminum metal addition with continuous stirring. The reaction mixture is then filtered to remove unreacted aluminum. The resultant solution contains about 64% peak 4 area and about 16% peak 3 area, as seen in FIG. 6. The filtered solution is then spray-dried using techniques described earlier. The resulting spray-dried powder contains 20.75±0.25% aluminum and 7.25±0.27% nitrogen, and a 15% solution in deionized water exhibits a pH range of 4.21–4.39. The HPLC chromatogram of a 10% solution of the spray-dried material contains 60–63% peak 4 area, 18–22% peak 3 area and no earlier chromatographic peaks corresponding to polymers of a larger molecular size. A total of 44 grams of aluminum metal reacted. The ferron reaction results in 11.5% $Al^a$, 40.6% $Al^b$ and 47.8% $Al^c$.

EXAMPLE 5

Figure 7:
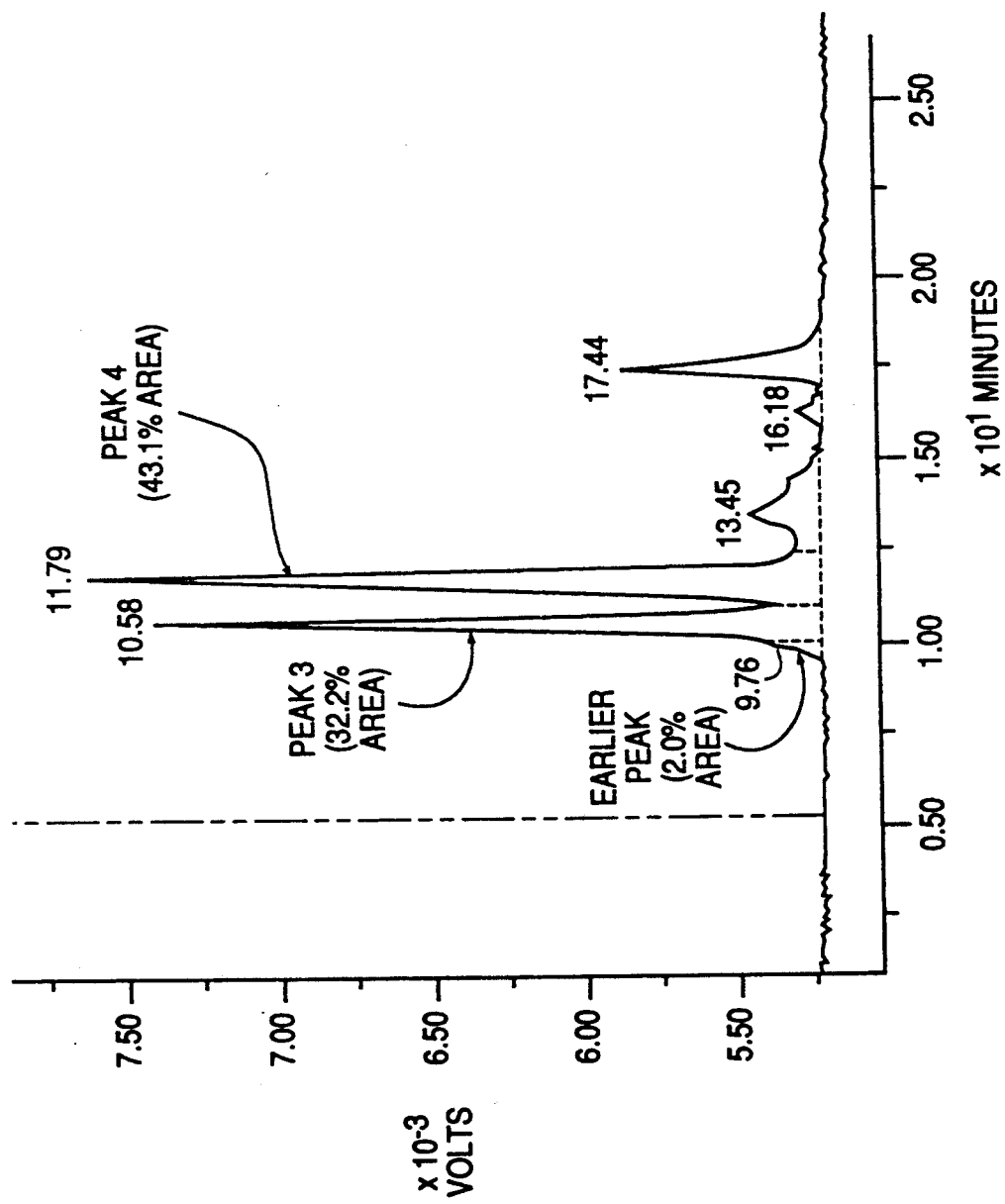
Figure 8:
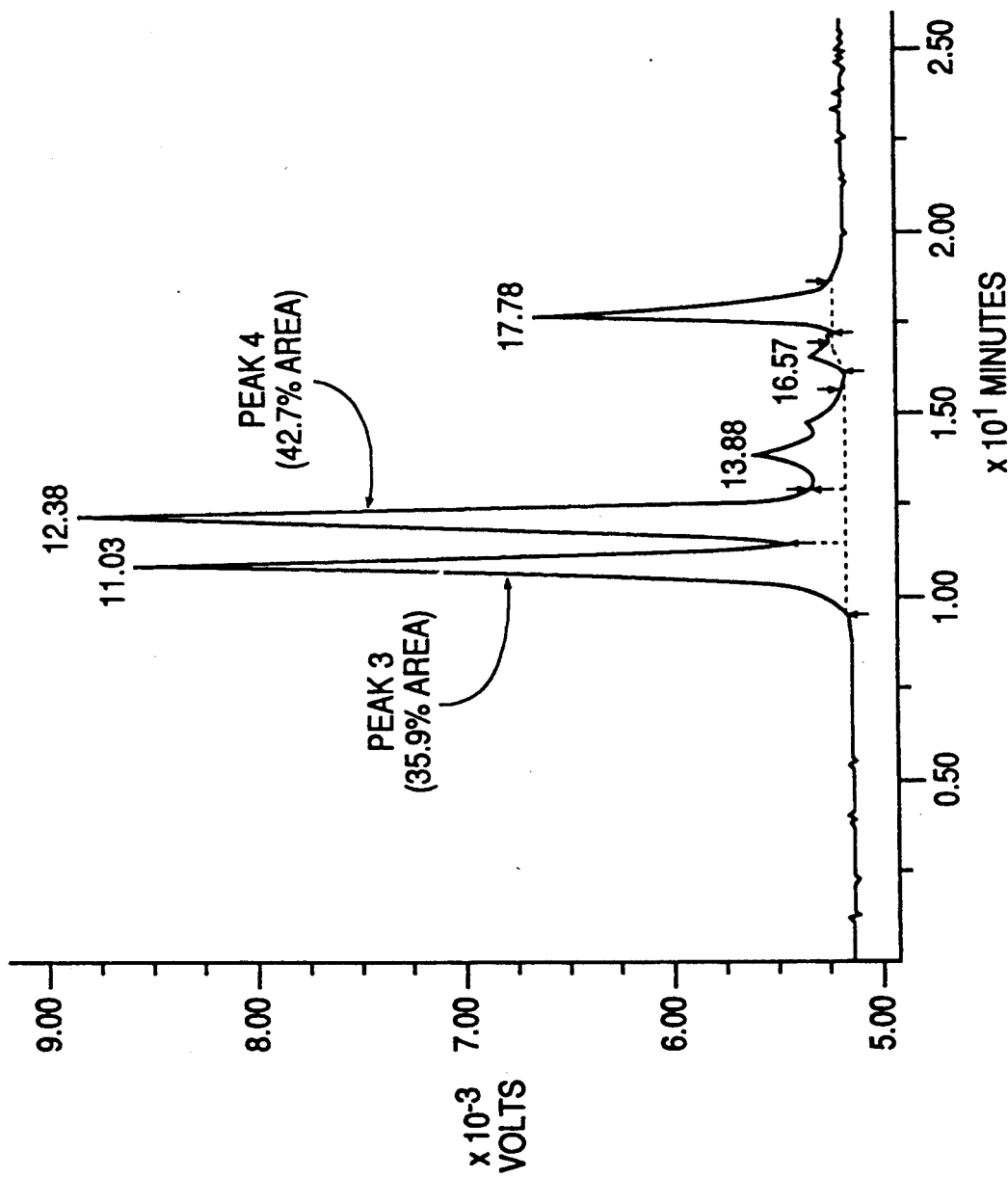
Figure 9:
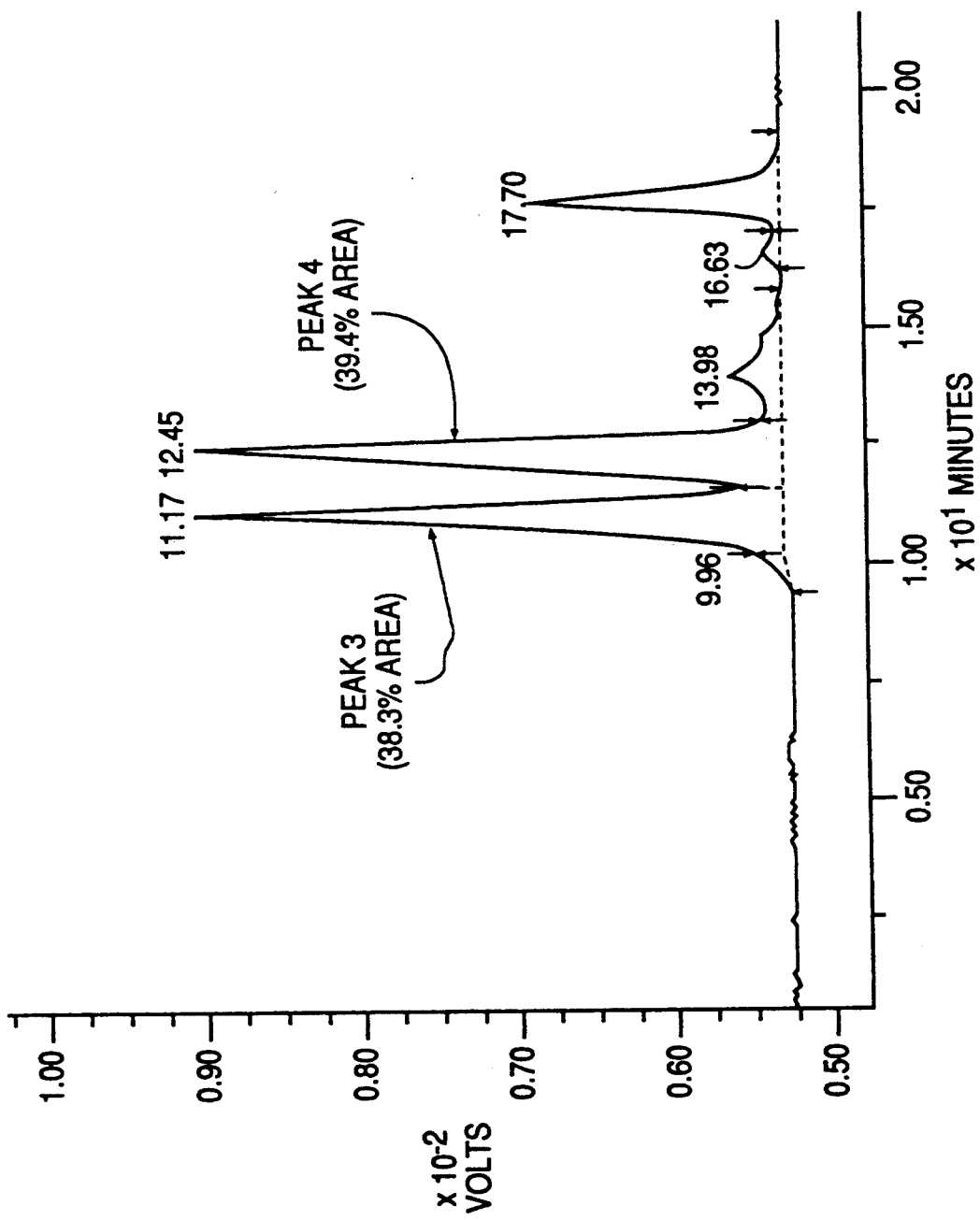
Figure 10:
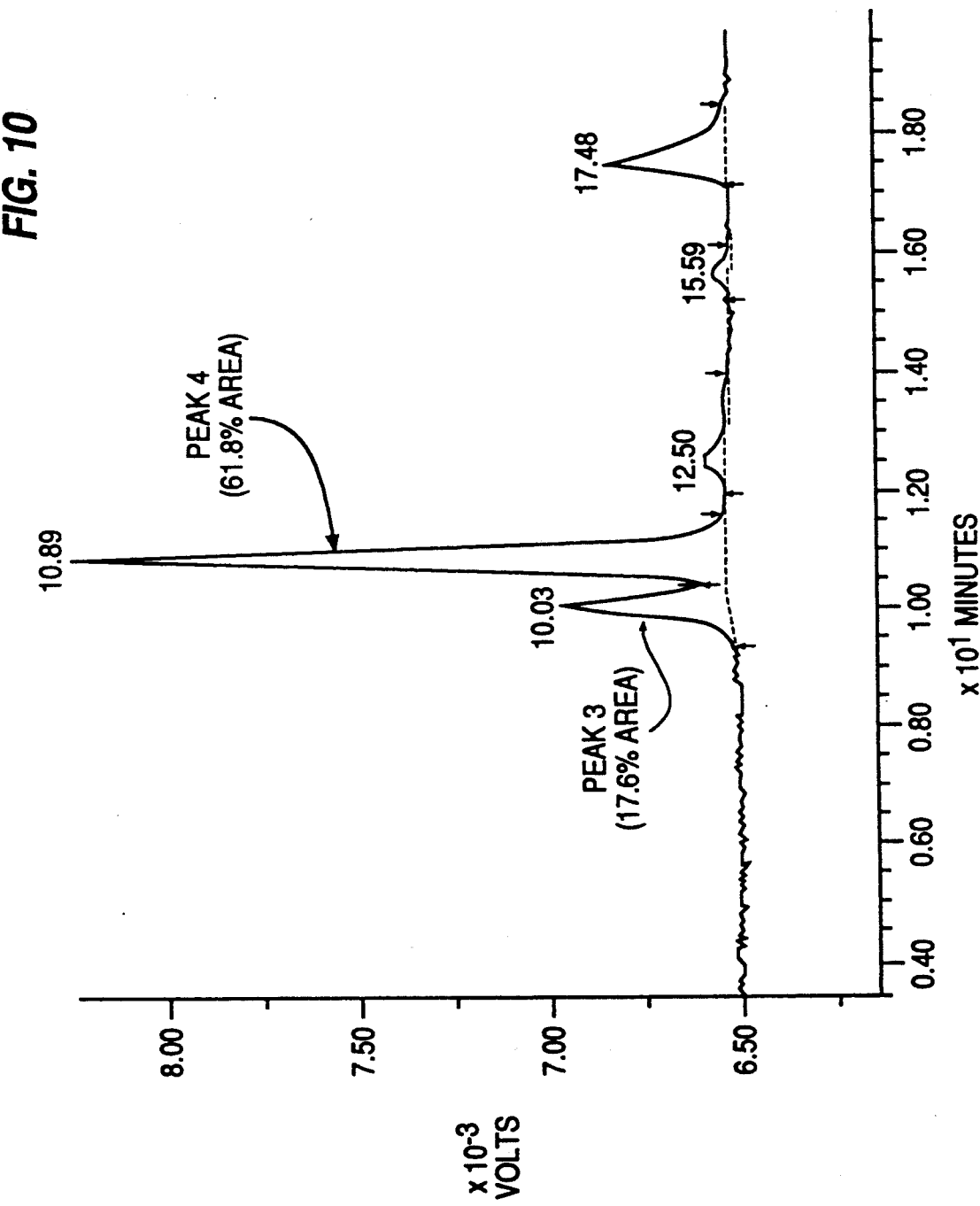

69.9 grams of aluminum nitrate nonahydrate are dissolved in deionized water to give 248.4 grams of total solution. The resultant 0.75M solution is heated to 75° C. over two hours. 50.18 grams of aluminum metal (small turnings) are added over a two minute period with continuous stirring. The reaction temperature is maintained at 75° C.–80° C. for a total period of three hours and forty-five minutes following the addition of aluminum metal. The reaction mixture was filtered to remove unreacted aluminum. A total of 8.87 grams of aluminum metal reacted. The filtrate was allowed to stand at room temperature for eighteen hours. The resultant solution is spray-dried with an inlet temperature of 205° C. and an outlet temperature of 95° C. The spray-dried powder contains 19.40% aluminum and 7.41% nitrogen. A 10% solution of the spray-dried powder contains 43% peak 4 area, 32% peak 3 area, and 2% of a peak corresponding to larger molecular weight polymers, as seen in FIG. 7. A 20% solution of the spray-dried powder, aged for thirty-seven days at room temperature, contains about 43% peak 4 area and about 36% peak 3 area, as shown in FIG. 8. After aging at room temperature for sixty-six days, the 20% solution contains about 39% peak 4 area and about 38% peak 3 area, as shown in FIG. 9. After aging at room temperature for 105 days, the 20% solution contains about 33% peak 4 and about 49% peak 3. After 110 days aging at room temperature, a 10% solution of the spray-dried powder contains about 62% peak 4 area and about 8% peak 3 area, as seen in FIG. 10. The ferron reaction results in 16.5% $Al^a$, 44.0% $Al^b$ and 39.5% $Al^c$.

EXAMPLE 6

Figure 11:
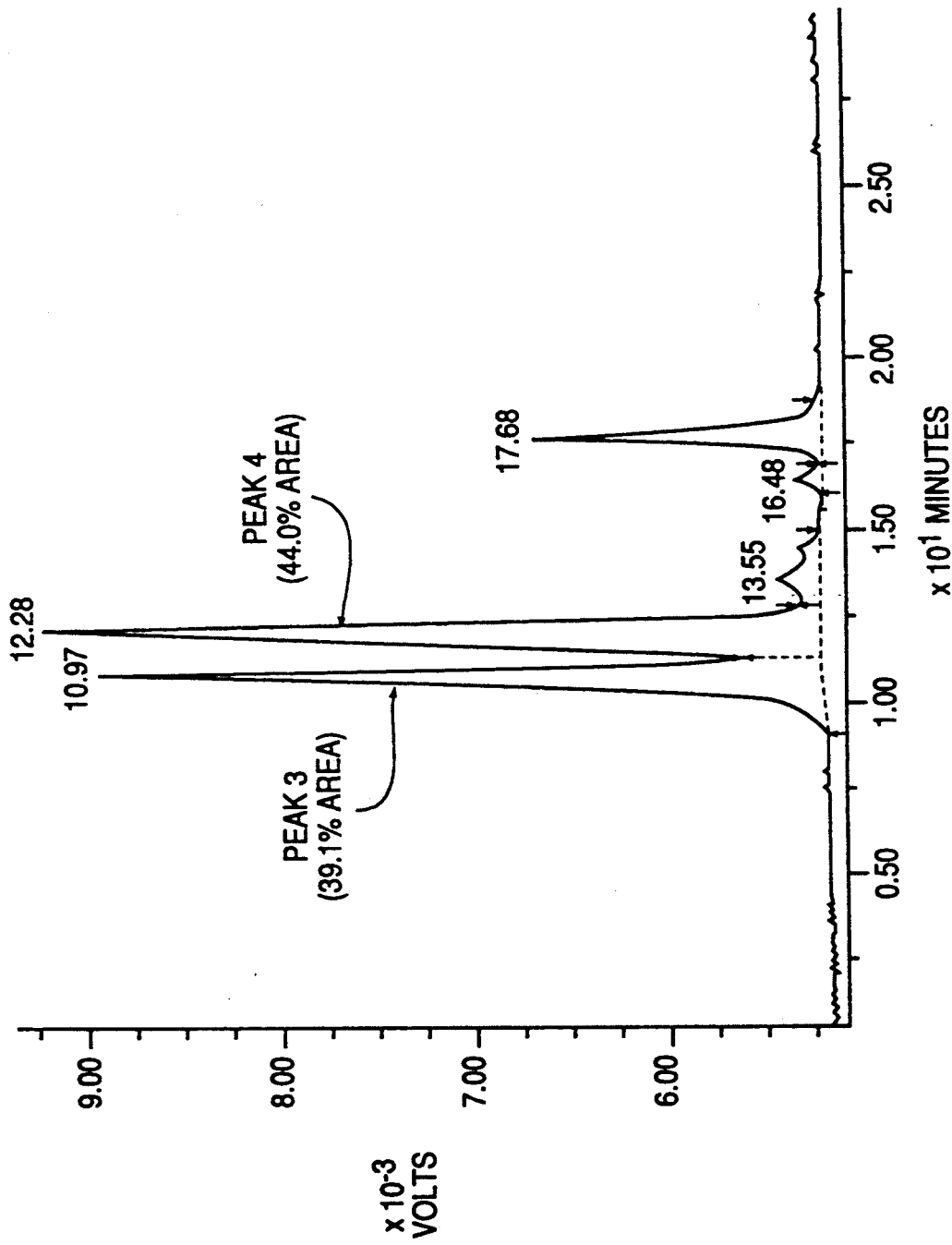
Figure 12:
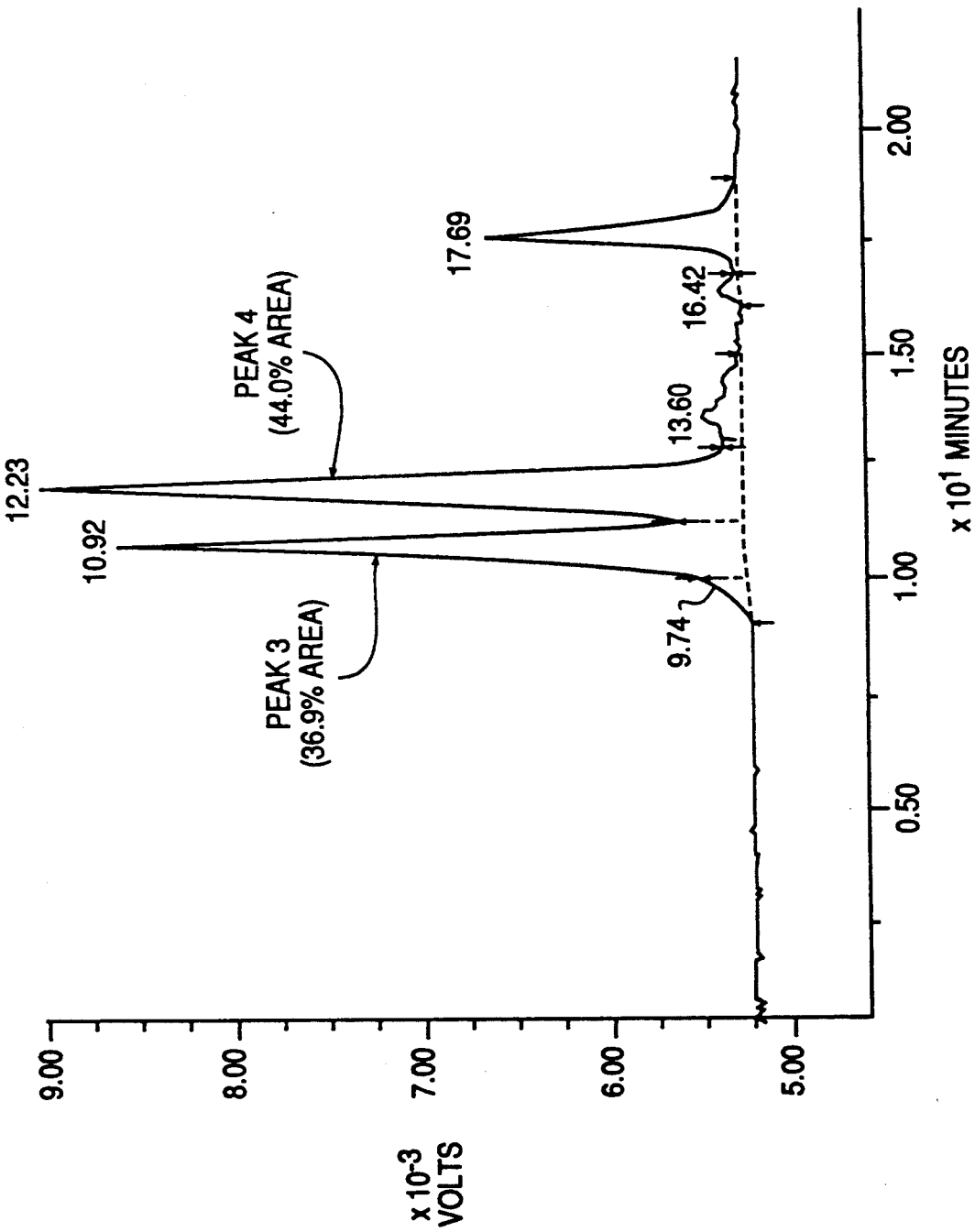
Figure 13:
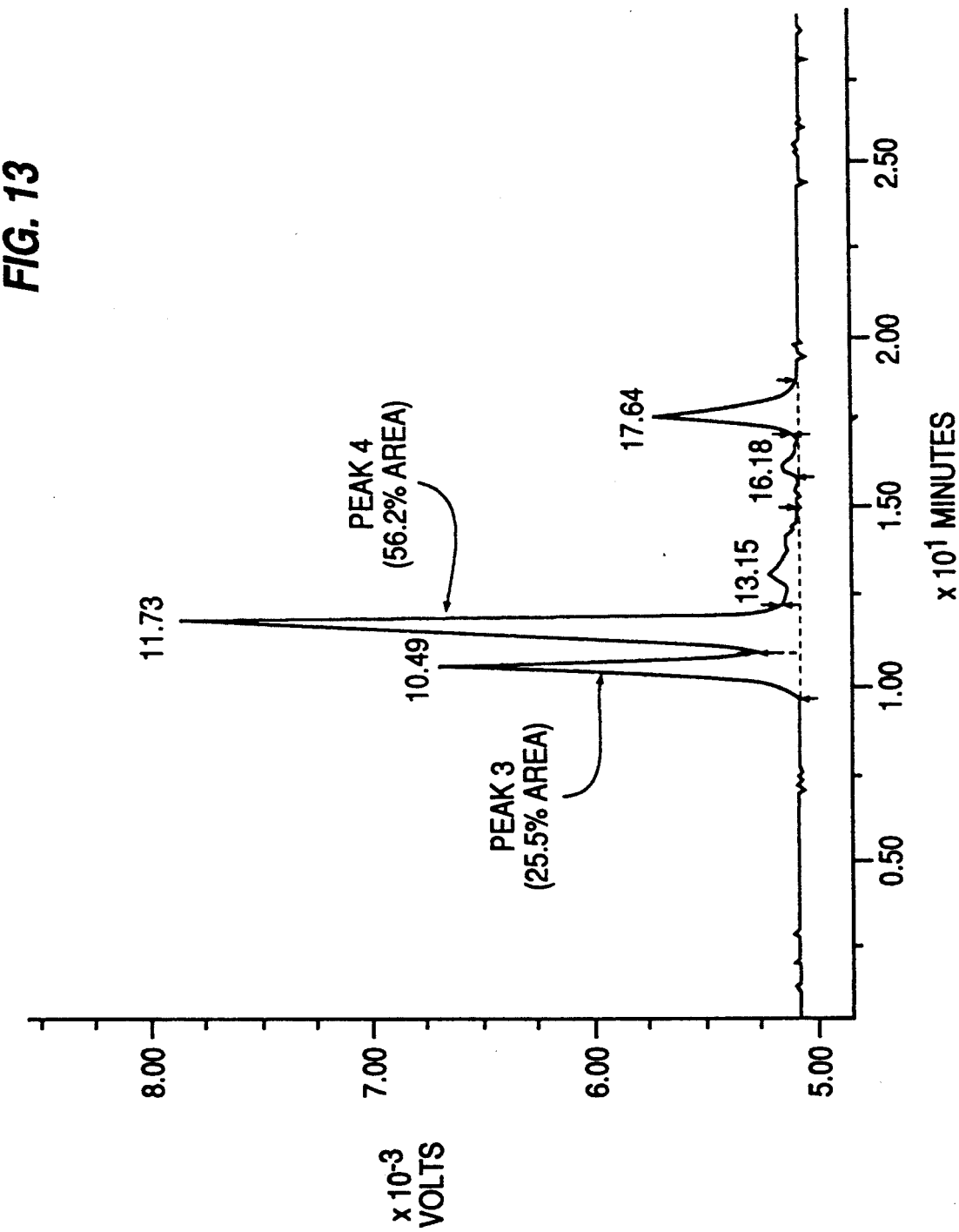

69.9 grams of aluminum nitrate nonahydrate are dissolved in deionized water to make 248.4 grams of total solution. The resultant 0.75M solution is heated to 70° C. 50.18 grams of aluminum metal are added with continuous stirring. The reaction mixture is maintained at a temperature of 70° C.–80° C. for a total of three and one-half hours following addition of the aluminum metal. The reaction mixture is quickly filtered to remove unreacted aluminum, and spray-dried immediately after filtration. A total of 9.3 grams of aluminum metal reacted. The resultant spray-dried powder contains 19.80% aluminum and 6.05% nitrogen. A 15% aqueous solution exhibits a pH of 4.23. A 10% solution of the spray-dried powder contains about 56% peak 4 area and about 25% peak 3 area. 10% and 20% solutions of the spray-dried powder aged sixty-one days at room temperature contain 44% peak 4 area, and about 39% and 37% peak 3 area, respectively. Note, respectively, FIGS. 11 and 12 for the size exclusion chromatograms of the 10% and 20% solutions of the spray-dried powder aged sixty-one days, and note FIG. 13 for the 10% solution of the spray-dried powder. The ferron reaction results in 13.5% $Al^a$, 30.3% $Al^b$ and 56.2% $Al^c$.

COMPARATIVE EXAMPLE 1

Figure 14:
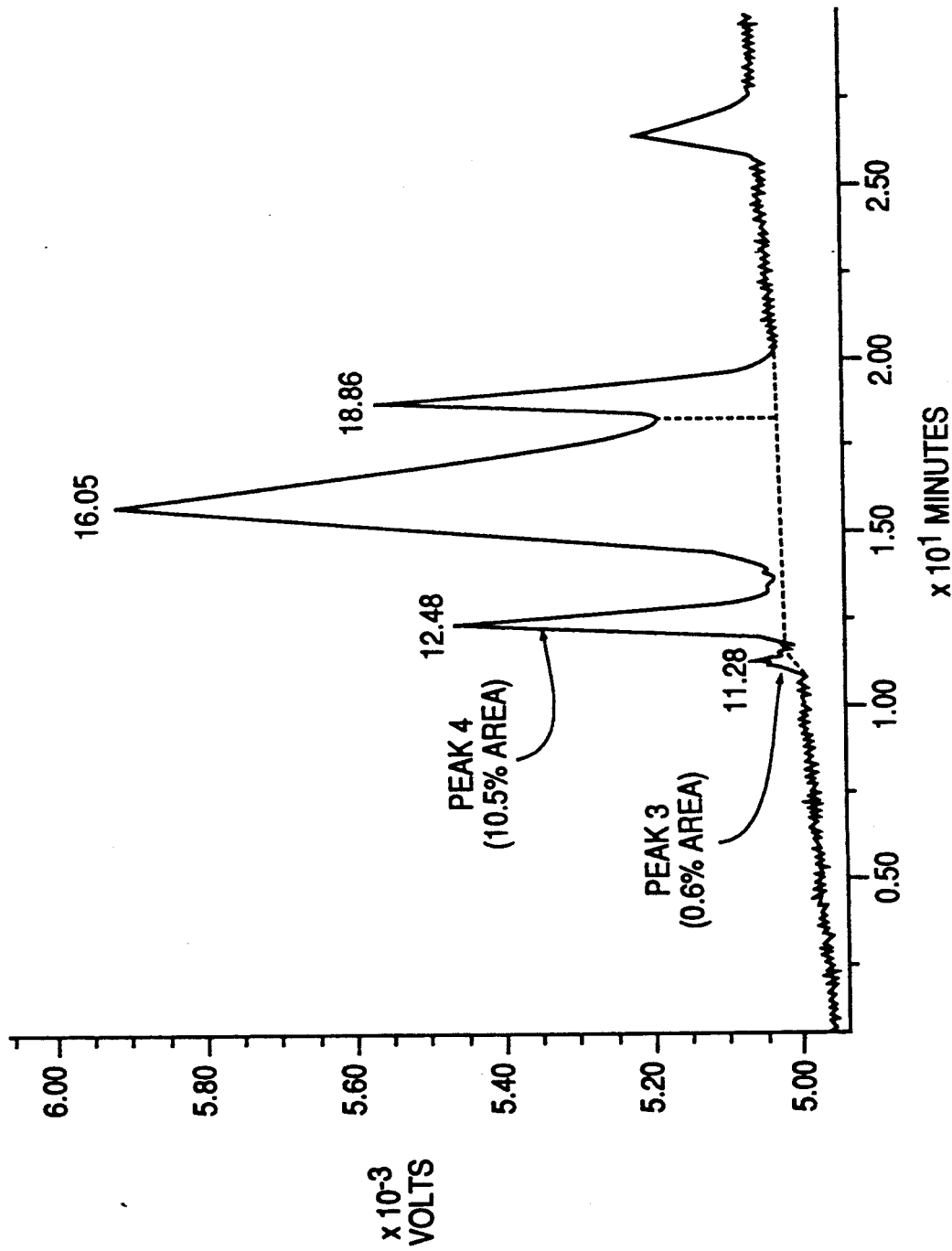
Figure 15:
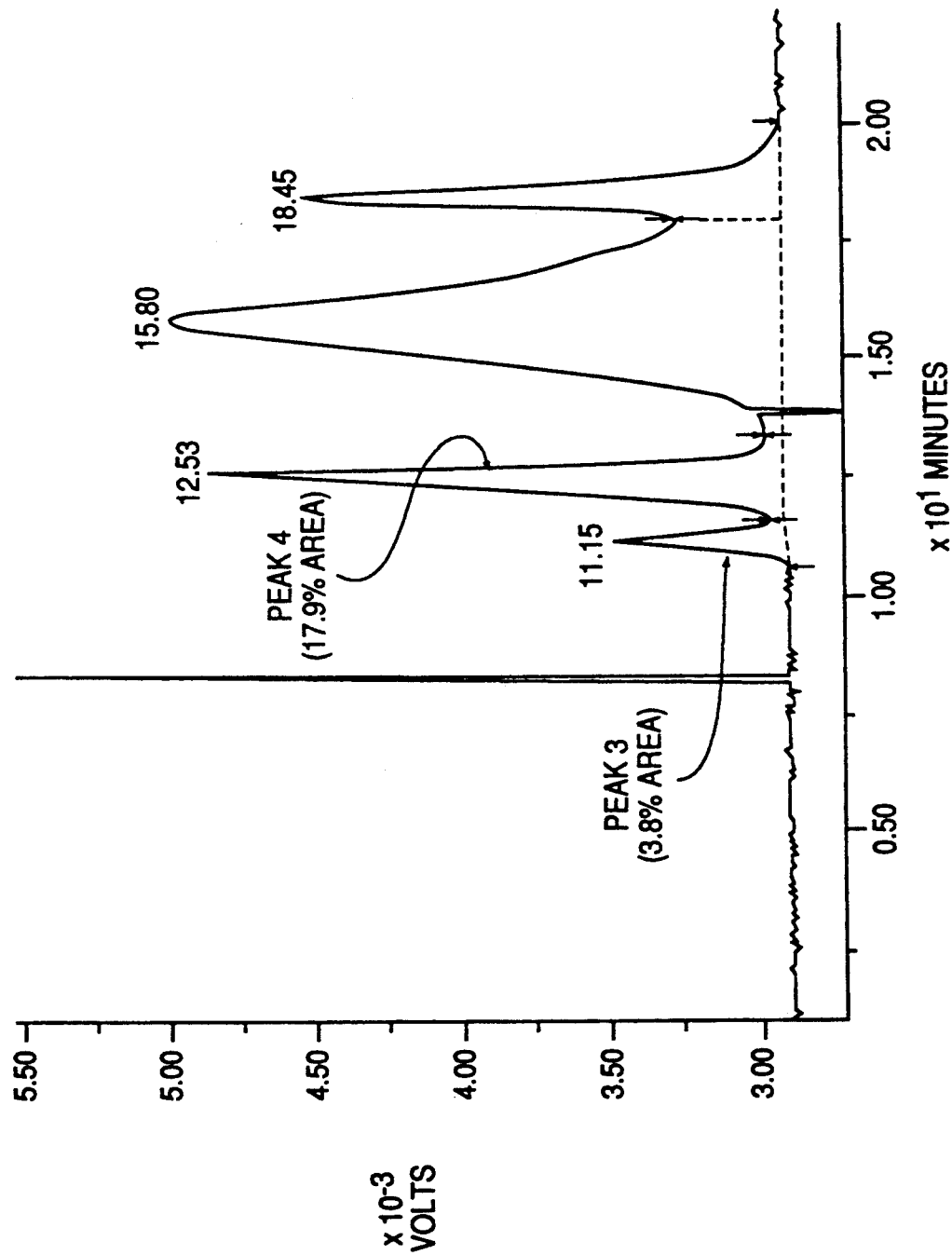
Figure 16:
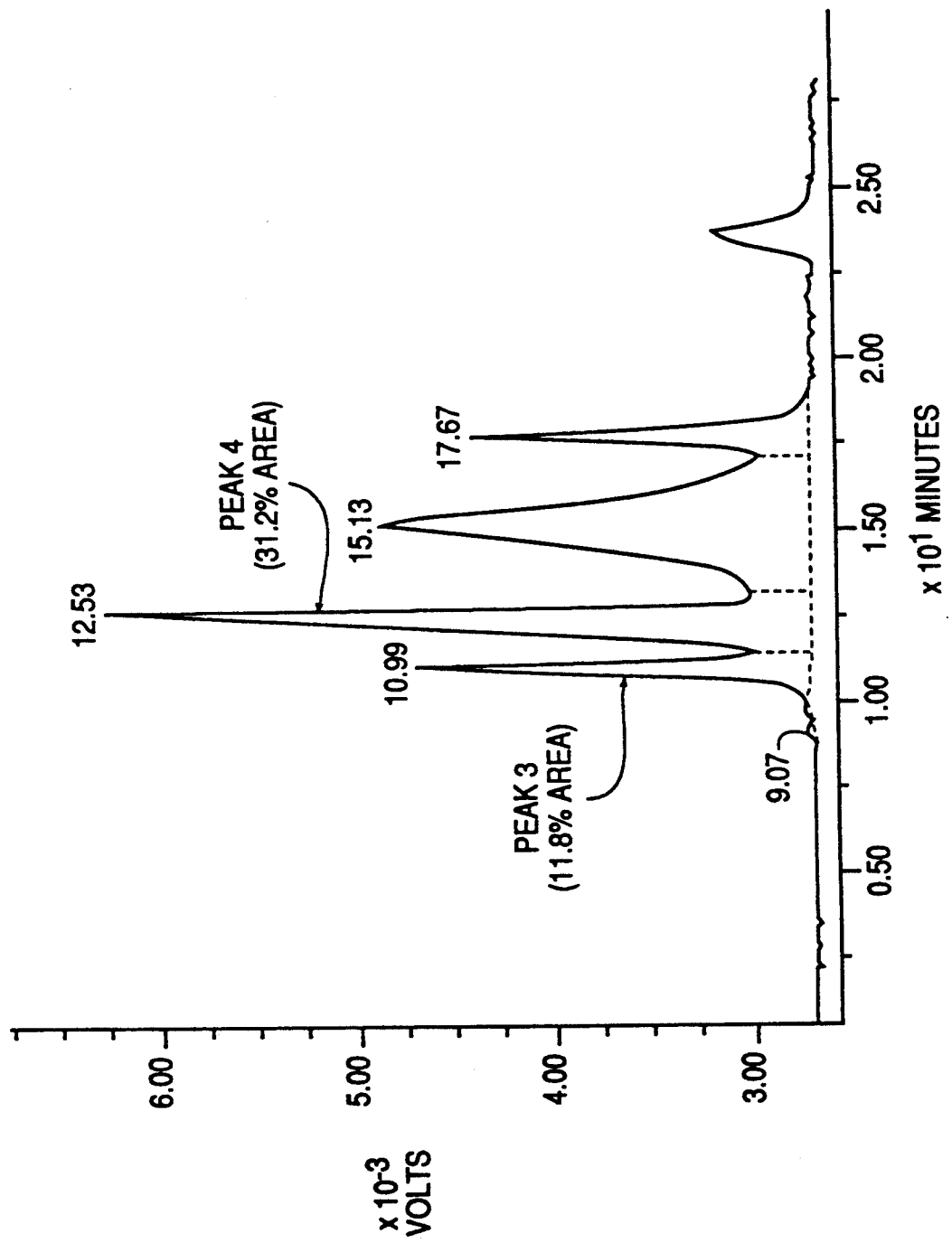

29.94 grams of aluminum chloride hexahydrate are dissolved in deionized water to give 248.6 grams of total solution. The resultant 0.5M solution is warmed to 37° C. over a two hour period. 33.52 grams of aluminum metal (small turnings) are added over two minutes. The reaction temperature is raised to 45° C. over a two hour period, and this temperature is maintained at 45° C.–50° C. with continuous stirring for a total of fourteen hours from aluminum chloride hexahydrate dissolution. Aliquots of the resulting supernatent solution are found to exhibit a relative HPLC size exclusion chromatographic peak 4 area of 10% and a peak 3 area of 1%, while about 90% of the chromatogram resembles the starting material. The reaction mixture was allowed to cool to room temperature by removing the heating mantle, and kept at room temperature for eleven and one-half hours. The chromatographic profile of the supernatent solution does not change at all during this eleven and one-half hour period, appearing practically identical to the chromatogram taken eleven and one-half hours earlier with about 10% peak 4 area and 0.6% peak 3 area, as seen in FIG. 14. The reaction mixture is then reheated to 45° C. over a thirty minute to forty-five minute period, and the temperature is maintained at 45° C.-50° C. for another seven hours with continuous stirring. Aliquots of the supernatent solution exhibited an HPLC peak 4 area of about 18% and a peak 3 area of about 4%, as seen in FIG. 15. After cooling to room temperature and storage for two days at room temperature, the reaction is reheated to 45° C.-50° C. again and maintained at this temperature with continuous stirring for another eight and one-half hours. The reaction mixture is filtered to remove unreacted aluminum and the resultant solution, after twenty-nine and one-half hours heating at 45° C.-50° C., exhibits a pH of 3.4 and contains about 31% peak 4 area and about 12% peak 3 area, as seen in FIG. 16. A total of 14.61 grams of aluminum reacted.

COMPARATIVE EXAMPLE 2

Figure 17:
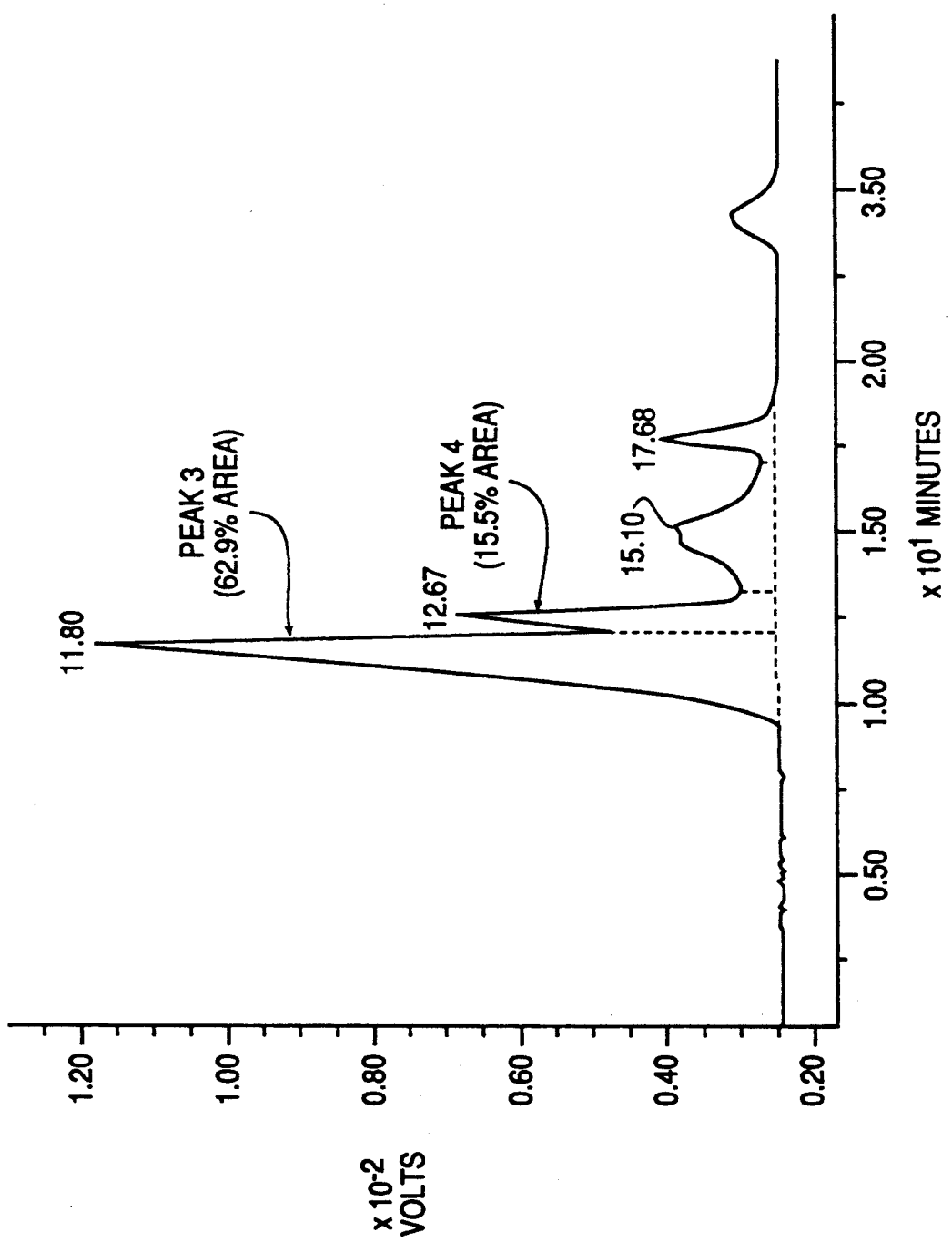
Figure 18:
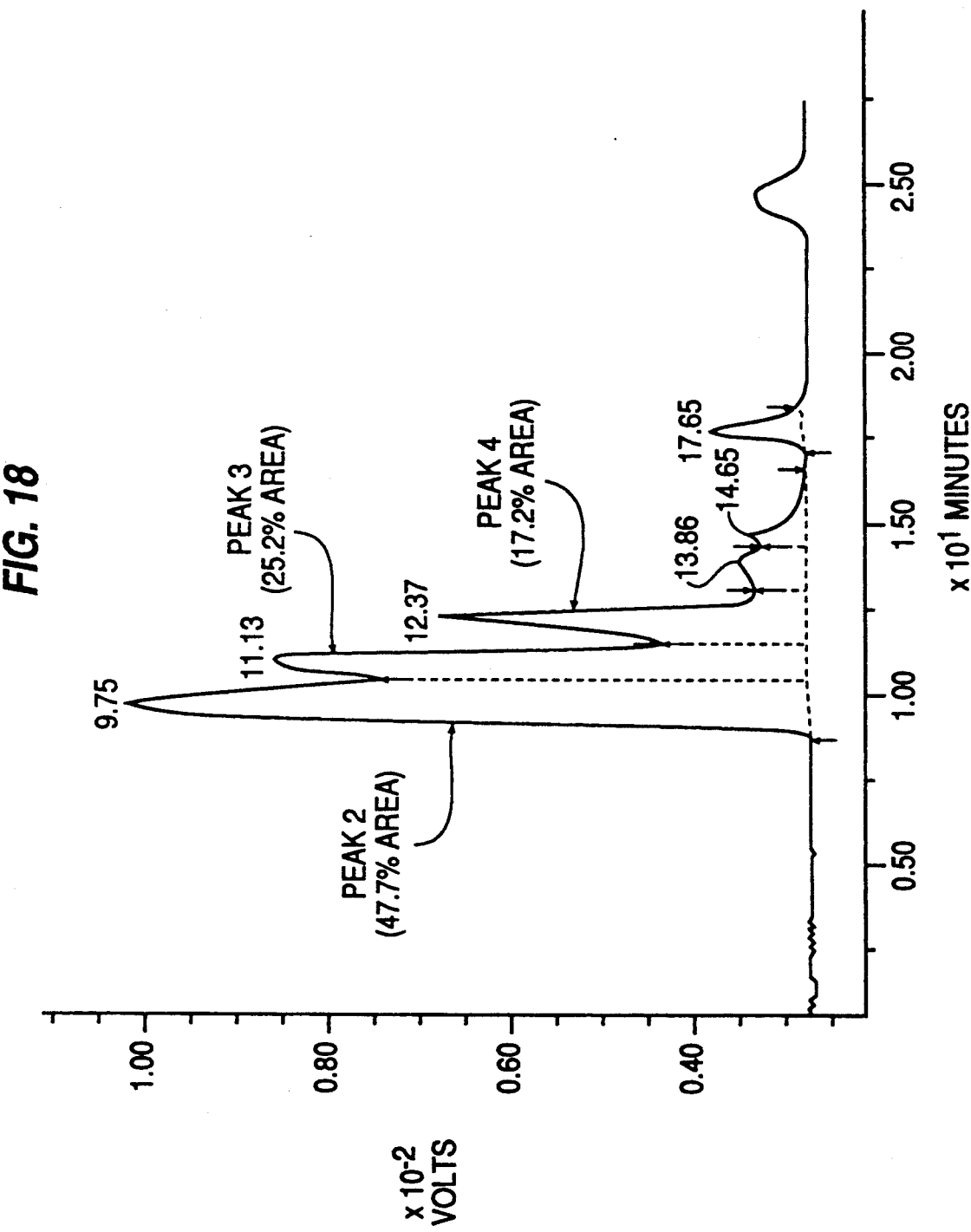

44.91 grams of aluminum chloride hexahydrate are dissolved in deionized water to give 248.6 grams of total solution. The resultant 0.75M solution is heated to 73° C. over a ninety minute period. 50.28 grams of aluminum metal (small turnings) is added over two minutes. The reaction temperature is maintained at 70° C.-78° C. with continuous stirring for a total of twelve hours. The reaction is then cooled to room temperature rapidly. Aliquots of the supernatent solution exhibit an HPLC size exclusion chromatographic peak 4 area of 15.5% and a peak 3 area of about 63%, as seen in FIG. 17. The reaction mixture is left at room temperature overnight and reheated to 70° C.-76° C. for an additional six hours. The reaction mixture is filtered to remove unreacted aluminum and the resultant solution, after eighteen hours at 70° C.-78° C., exhibits a peak 4 area of about 17%, a peak 3 area of about 25% and a larger, earlier peak 2 area of about 48%, the total peak 3 area plus peak 4 area being 42%, as seen in FIG. 18. A total of 25.28 grams of aluminum reacted.

COMPARATIVE EXAMPLE 3

Figure 19:
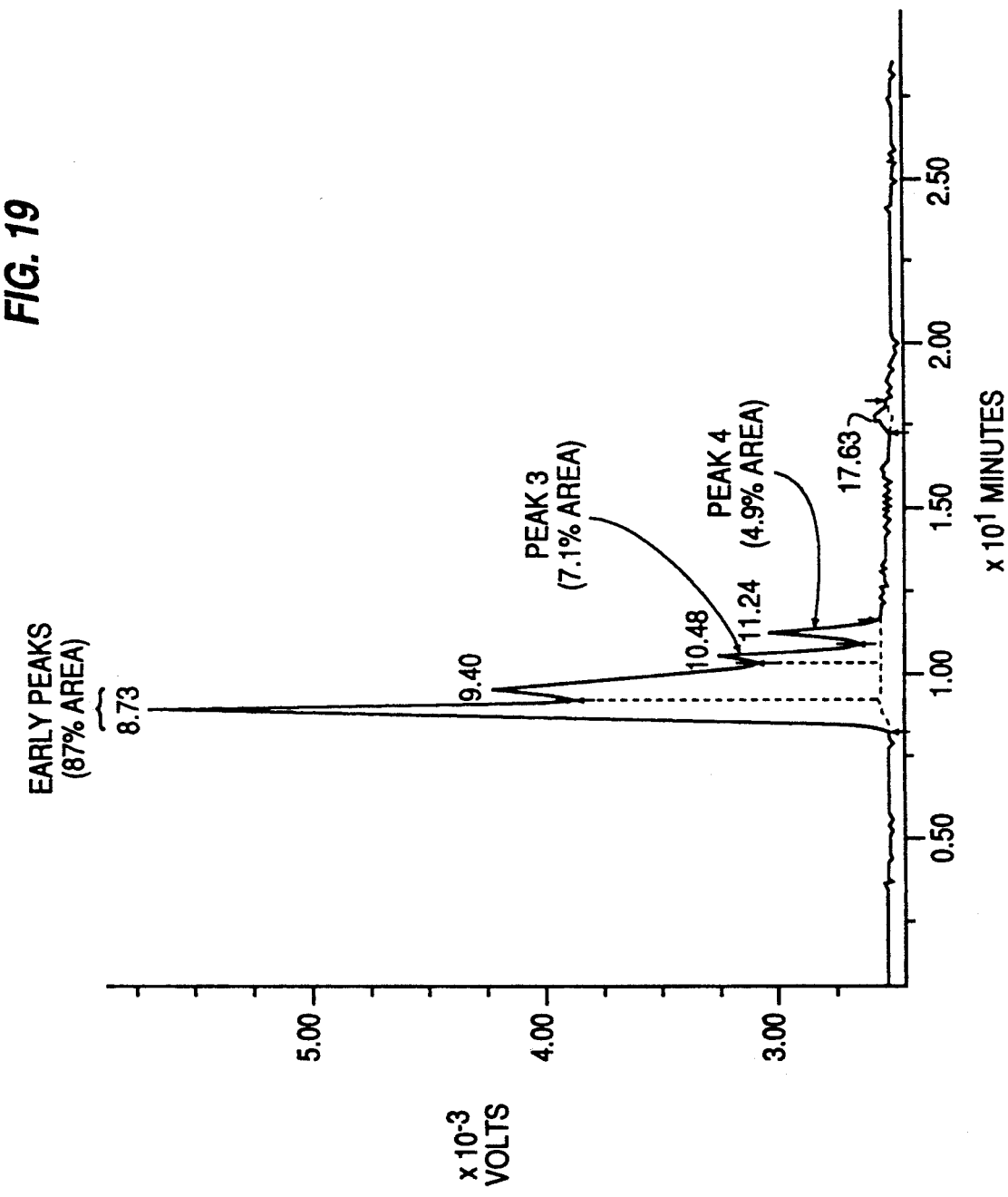

Example 14 of British Patent Specification No. 1,568,831 was prepared as follows: 37.4 grams of aluminum nitrate nonahydrate are dissolved in deionized water to give 200 grams of total solution. The resultant 0.5M solution is heated to 90° C., and 13.45 grams of atomized aluminum metal (Reynolds LSA-29-atomized) is added over the next five hours at a temperature of 89° C.-97° C. with continuous stirring. The reaction mixture is maintained at 88° C.-91° C. for another twenty-four hours. The resultant reaction mixture is quite viscous and impossible to filter to remove the unreacted aluminum. An aliquot of the reaction mixture is diluted and found to contain about 5% peak 4 area, about 7% peak 3 area and 87% of the total peak area representing several peaks of larger molecular weight than peaks 3 or 4, as seen in FIG. 19. The ferron reaction result in 2% $Al^a$, 5% $Al^b$ and 93% $Al^c$.

Figure 20:
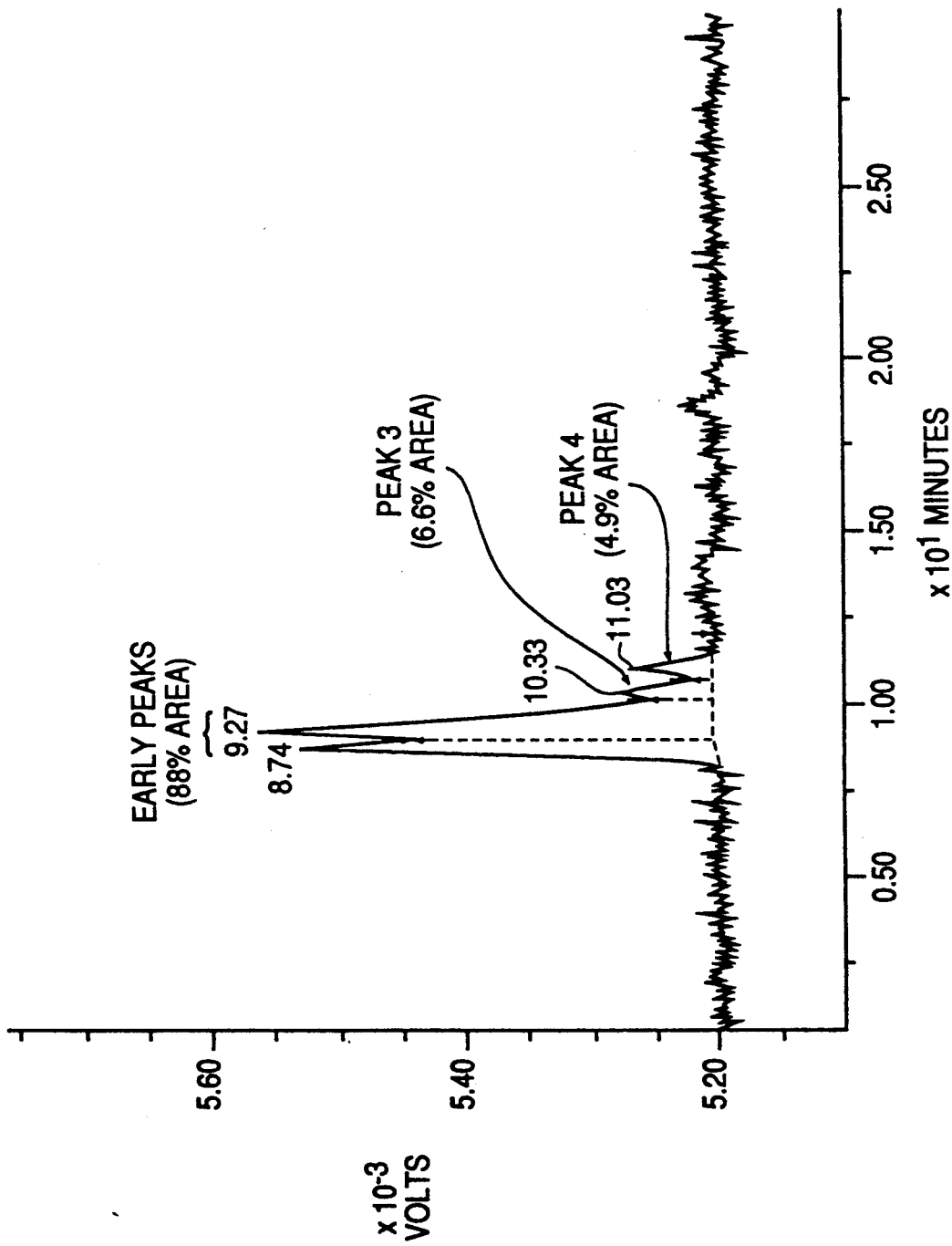

The HPLC chromatogram of the resultant solution aged three months at room temperature contains about 5% peak 4 area, about 7% peak 3 area and about 88% of the total peak area corresponding to several peaks of larger molecular weight than peaks 3 or 4, as seen in FIG. 20.

EXAMPLE 7

Figure 21:
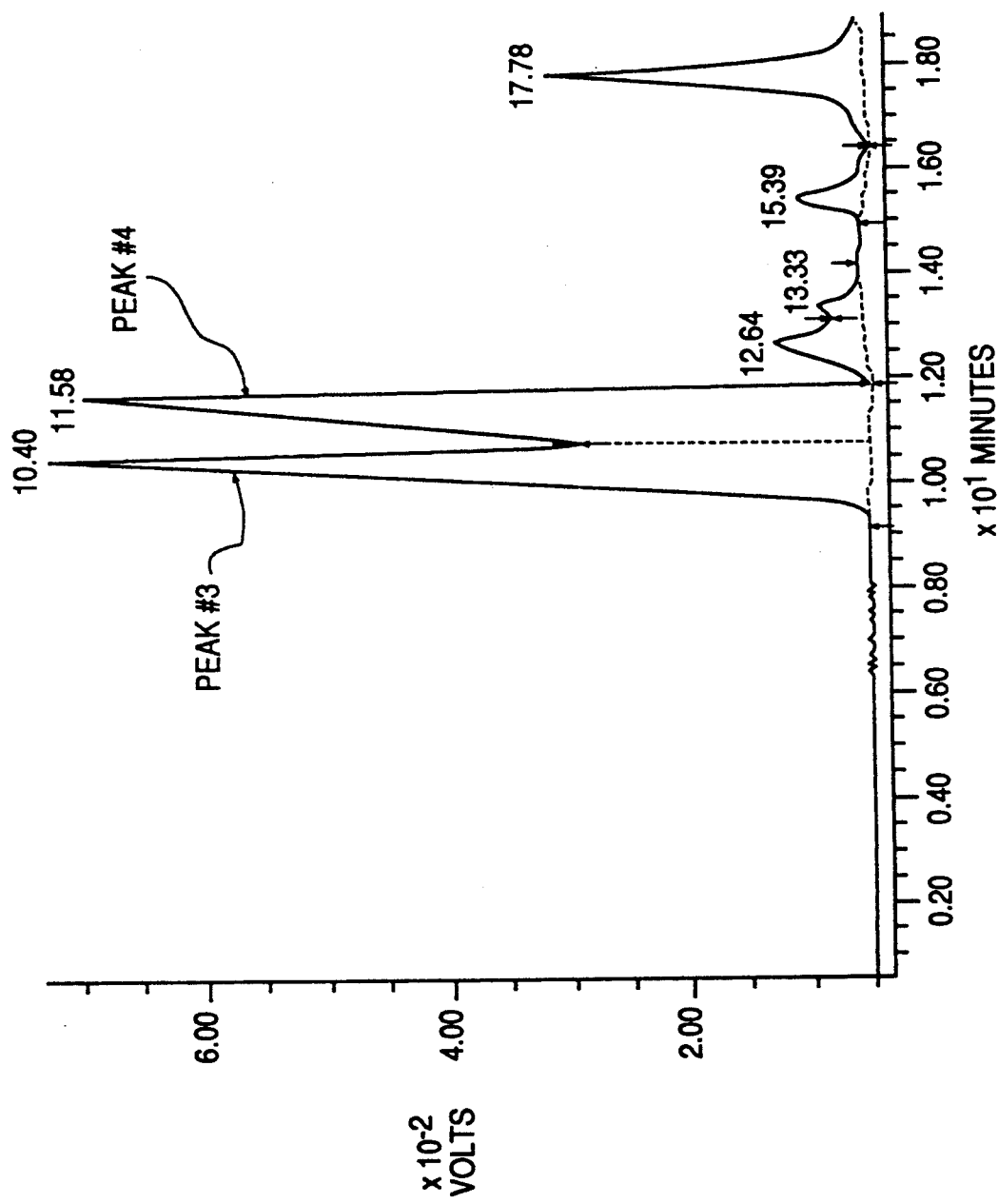

139.5 grams of aluminum nitrate nonahydrate are dissolved in deionized water to give 318.0 grams of total solution. The resulting 1.17M solution is heated to 80°-85° C. over a 30 minute period. 50.2 grams of aluminum metal (small turnings) are added over two minutes. The reaction temperature is raised to 85°-90° C., and maintained at this temperature with continuous stirring. After a total of 3.5 hours from the addition of the aluminum metal, the temperature is raised to 95°-100° C. for thirty minutes. After a total of four hours from the addition of the aluminum metal, the reaction mixture is filtered hot to remove unreacted aluminum. The resultant solution contains 40.6% peak 3 area, 40.8% peak 4 area, and no earlier chromatographic peaks, as shown in FIG. 21. A total of 22 grams of aluminum metal reacted. The solution is then spray-dried or freeze-dried, using the techniques disclosed previously herein.

The following examples describe forming the antiperspirant active composition according to the present invention. In Example 8, the composition is formed using the more acidic $ZrO(NO_3)_2$. In Example 10, the active composition is formed at a relatively high temperature (as compared to room temperature).

EXAMPLE 8

Figure 22:
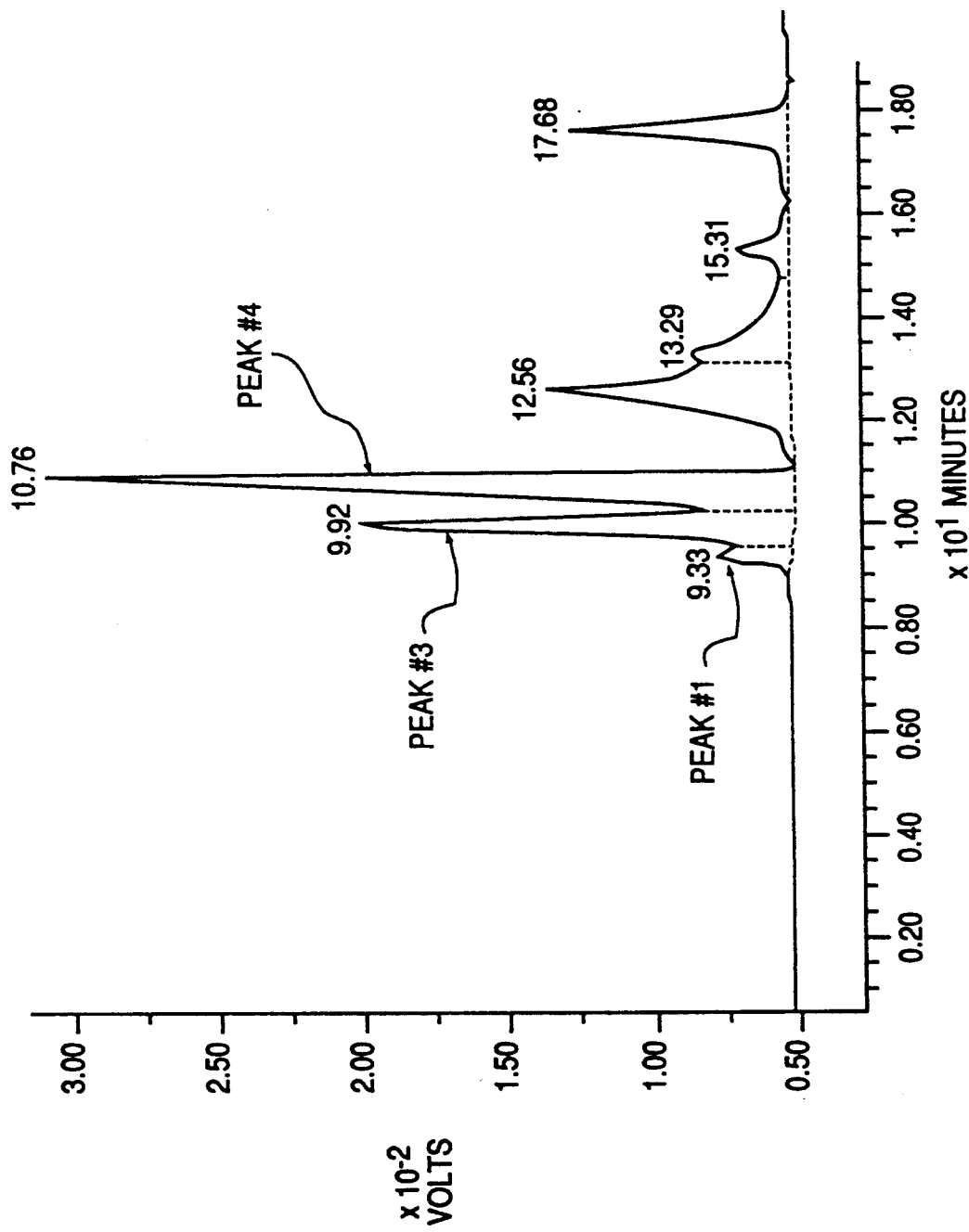

12.86 grams of aluminum nitratohydrate powder corresponding to the present invention, 16.93 grams of a 37.5% aqueous solution of zirconyl oxynitrate ($ZrO(NO_3)_2$, 2.0 grams of glycine and 18.36 grams of water were combined together and stirred for 15 minutes at room temperature to form a solution of aluminum/zirconium nitratohydrex-glycine. FIG. 22 shows the size exclusion chromatogram for the aluminum/zirconium nitratohydrexglycine composition according to this Example. The relative peak 4 area is 34.8% and the relative area of peak 3 is 18.7%.

EXAMPLE 9

50 grams of $ZrO(OH) (CO_3)_{0.5}$ (zirconium basic carbonate) solid is slowly added to 14.6 grams of concentrated nitric acid with constant stirring. The reaction is exothermic. The resultant solution is placed through an ultrasonicator three times for a total of 30 minutes, stirring in between each pass. The resultant zirconyl hydroxynitrate solution is stirred for an additional 15 minutes at room temperature. Elemental analysis of the resultant zirconyl hydroxynitrate ($ZrO(OH)NO_3$) solution yielded 24.8% zirconium and 3.8% nitrogen.

Figure 23:
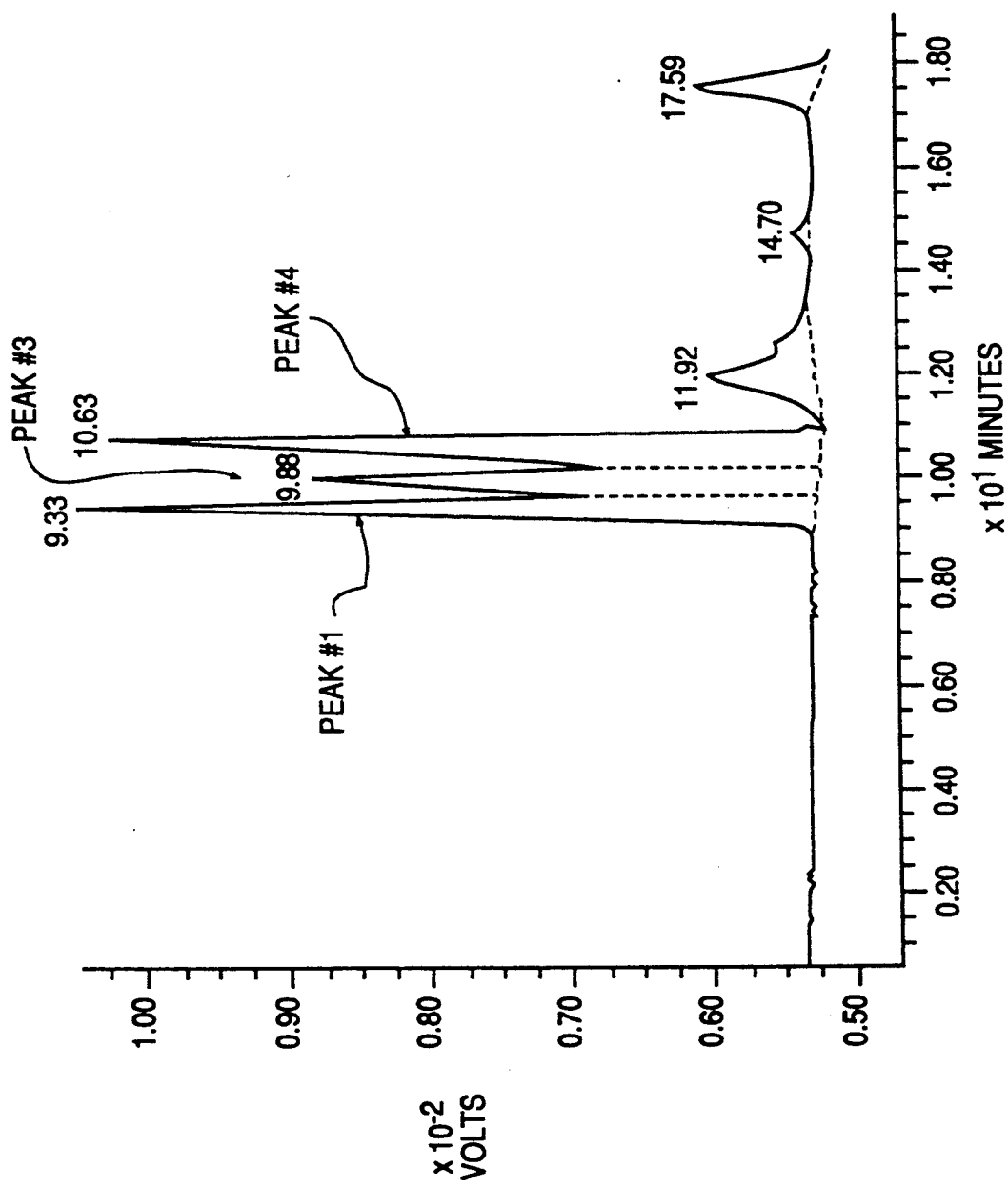

14.94 grams of aluminum nitratohydrate, 11.82 grams of the zirconyl hydroxynitrate solution prepared above, 2.44 grams of glycine and 37.14 grams of water are combined together at room temperature and stirred until completely dissolved. The resulting 35% solution of aluminum/zirconium nitratohydrex-glycine is passed through an ultrasonicator for 5 minutes. The resultant solution is spray-dried. The powder was analyzed to contain 9.8% zirconium, 11.46% aluminum and 7.75% nitrogen and a 15% aqueous solution exhibited a pH of 4.00. The size exclusion chromatogram of the zirconium/aluminum nitratohydrate of this Example is shown in FIG. 23. The relative peak 3 area is 22.9% and the relative peak 4 area is 35.5%.

EXAMPLE 10

The same combination of ingredients as in Example 9 was prepared, except that the aluminum nitratohydrate, zirconyl hydroxynitrate and glycine solution was heated at 89° C. for one-half hour and diluted to 10%, instead of room temperature preparation at 35%. FIG. 24 shows the size exclusion chromatogram of this composition. The peak 3 relative area is 2.3%, the peak 4 relative area is 51.7% and the peak 1 relative area is 28.1%.

As seen in the Examples and Comparative Examples, the present invention provides the advantageous result of forming a basic aluminum material, utilizing anions such as nitrate, for example, which basic aluminum material can be formed at significantly faster reaction rates and at temperatures lower than that utilized for forming conventional aluminum halide materials with enhanced activity. Furthermore, the basic aluminum material with enhanced antiperspirant activity of the present invention can be formed more rapidly and at lower temperatures than even conventional, non-enhanced activity basic aluminum materials. Furthermore, according to the present invention antiperspirant compositions including a basic aluminum material and, e.g., a zirconium material, having enhanced activity, can be provided, at a relatively low temperatures, the compositions having relatively high stability. Moreover, the present invention, utilizing relatively low temperatures, forms a product with enhanced activity (increased peak 4 relative area) as compared to the basic aluminum compound formed utilizing the teachings of British Patent Specification No. 1,568,831.

Accordingly, by the present invention, utilizing anions and treatment as described in the foregoing, a basic aluminum material having enhanced antiperspirant activity can be made without need of high temperatures and/or diluted solutions, and the material formed has improved compositional stability in aqueous solution over a period of time. Moreover, such material can be incorporated in a composition together with zirconium, hafnium, tin and/or titanium active antiperspirant material and an optional neutral amino acid, to provide basic aluminum/zirconium, hafnium, tin and/or titanium compositions with enhanced antiperspirant activity.

Of particular significance, by the present invention, a basic aluminum material and compositions containing this material, with enhanced antiperspirant activity, can be formed at a significantly faster throughput or rate than conventional enhanced active or even non-enhanced active basic aluminum compounds; as can be appreciated, the faster throughput will lower the cost of manufacturing the antiperspirant.

Another advantage of the present invention is the ease with which basic aluminum materials and compositions containing such materials can be formed with peak 4 relative areas greater than 40% and up to 70%, which can result in basic antiperspirant materials of even greater antiperspirant activity than conventional enhanced activity antiperspirant materials.

While we have shown and described several embodiments in accordance with the present invention, it is understood that the same is not limited thereto, but is susceptible of numerous changes and modifications as known to those skilled in the art. Therefore, we do not wish to be limited to the details shown and described herein, but intend to cover all such changes and modifications as are encompassed by the scope of the appended claims.

What is claimed is:

1. An antiperspirant active composition comprising:
   (1) a basic aluminum material, with enhanced antiperspirant activity, having the empirical formula:

$$Al_2(OH)_{6-a}X_a,$$

where $0.5 \leq a \leq 5.0$ and X is an anion that is a univalent complex oxoanion of nitrogen or a halogen, which anion forms salts with $Al^{3+}$ in aqueous solution so that these salts are substantially completely disocciated, which anion is readily soluble in water with metallic ions in the solutions, and which anion forms conjugate acids that are strong acids; wherein said basic aluminum material is characterized by:
   (a) size exclusion high performance liquid chromatography peaks corresponding to peak 3 and peak 4 of size exclusion chromatograms formed by HPLC technique;
   (b) a peak 4 relative area of at least 25%, a peak 3 relative area of less than 60%, the sum of the relative peak 3 and peak 4 areas being at least 50%;
   (c) less than 10% chromatographic peaks eluting at shorter retention times than peak 3, corresponding to peaks 1 and 2; and
   (2) an antiperspirant active material containing a metal cation selected from the group consisting of Zr, Hf, Ti and Sn.

2. An antiperspirant active composition according to claim 1, wherein the composition comprises:

$$[Al_2(OH)_{6-a}(X)_a]_w[DO_p(OH)_mQ_n]_y[(neutral\ amino\ acid)]_z,$$

where a and X are as defined previously; w:y ranges from 0.3:1 to 6.0:1; z:y ranges from 0 to 1.3:1; p is either 0 or 1, where when p=0 then m=0 and n=4, and when p=1 then m+n=2; D is a metal cation selected from the group consisting of Zr, Hf, Ti and Sn; and Q is a halide or said univalent complex oxoanion.

3. An antiperspirant active composition according to claim 2 wherein X is selected from the group consisting of $ClO_3^-$, $ClO_4^-$, $IO_4^-$, and $NO_3^-$.

4. An antiperspirant active composition according to claim 2, wherein X is $NO_3^-$.

5. An antiperspirant active composition according to claim 2, wherein the composition is further characterized by size exclusion high performance liquid chromatography peaks corresponding to peak 3 and peak 4 of size exclusion chromatograms formed by HPLC technique, with a peak 4 relative area of at least 25% and a peak 3 relative area of less than 50%.

6. An antiperspirant active composition according to claim 2, wherein w:y ranges from 0.3:1 to 2.0:1.

7. An antiperspirant active composition according to claim 6 wherein the peak 4 relative area is at least 25% and the peak 3 relative area is less than 15%.

8. An aqueous solution comprising the antiperspirant composition according to claim 1 dissolved in water.

9. A dried powder of said antiperspirant active composition of claim 1.

10. An antiperspirant active composition according to claim 1 wherein the anion is selected from the group consisting of $ClO_3^-$, $ClO_4^-$, $IO_4^-$ and $NO_3^-$.

11. An antiperspirant active composition according to claim 10 wherein the anion is $NO_3^-$.

12. An antiperspirant active composition according to claim 1, wherein the peak 4 relative area is at least 40% and the peak 3 relative area is less than 50%.

13. An antiperspirant active composition according to claim 1, wherein the composition further includes a neutral amino acid.

14. A method of forming an antiperspirant active composition, comprising mixing (1) an antiperspirant active material containing a metal cation selected from the group consisting of Zr, Hf, Ti and Sn, with (2) a basic aluminum material, with enhanced antiperspirant activity having the empirical formula:

$$Al_2(OH)_{6-a}X_a,$$

where $0.5 \leq a \leq 5.0$; and X is an anion that is a univalent complex oxoanion of nitrogen or a halogen, which anion forms salts with $Al^{3+}$ in aqueous solution so that these salts are substantially completely dissociated, which anion is readily soluble in water with metallic ions in the solutions, and which anion forms conjugate acids that are strong acids; wherein said basic aluminum material is characterized by:

(a) size exclusion high performance liquid chromatography peaks corresponding to peak 3 and peak 4 of size exclusion chromatograms formed by HPLC technique;

(b) a peak 4 relative area of at least 25%, a peak 3 relative area of less than 60%, and the sum of the relative peak 3 and peak 4 areas being at least 50%; and (c) less than 20% chromatographic peaks eluting at shorter retention times than peak 3, corresponding to peaks 1 and 2.

15. A method of forming an antiperspirant active composition according to claim 14, wherein said mixing is performed at room temperature.

16. A method of forming an antiperspirant active composition according to claim 14, wherein said basic aluminum material is formed by a process comprising the steps of:

(a') dissolving $Al(Y^wO_n)_3$ in water so as to form a solution, where Y is nitrogen or a halogen, w is the oxidation state of Y, and n is dependent on the oxidation state of Y; and (b') reacting aluminum metal with $Al(Y^wO_n)_3$ in solution so as to form a reaction product of $Al_2(OH)_{6-a}X_a$, the reaction being performed at a temperature, and for a time, such that the reaction product is characterized by:

(A) said size exclusion high performance liquid chromatography peaks corresponding to peak 3 and peak 4 of size exclusion chromatograms formed by HPLC technique;

(B) the peak 4 relative area of at least 25%, the peak 3 relative area of less than 60%, and the sum of the relative peak 3 and peak 4 areas being at least 50%; and (C) less than 10% chromatographic peaks eluting at shorter retention times than peak 3, corresponding to peaks 1 and 2.

17. A method of forming an antiperspirant active composition according to claim 16, wherein forming the basic aluminum material is performed at a temperature of 45° C.-100° C.

18. A method of forming an antiperspirant active composition according to claim 17, wherein forming the basic aluminum material is performed at a temperature of 45° C.-90° C.

19. A method of forming an antiperspirant active composition according to claim 16, wherein $Al(Y^wO)_3$ is prepared in situ from aluminum metal and an inorganic acid $HY^wO_n$.

20. A method of forming an antiperspirant active composition according to claim 15, wherein the mixing is performed at a temperature of 45° C.-140° C. for a time period of 0.5-17 hours.

21. An antiperspirant active composition comprising:

(1) a basic aluminum material, with enhanced antiperspirant activity, having the empirical formula:

$$Al_2(OH)_{6-a}X_a,$$

where $0.5 \leq a \leq 5.0$; and X is an anion that is a univalent complex oxoanion of nitrogen or a halogen, which anion forms salts with $Al^{3+}$ in aqueous solution so that these salts are substantially completely dissociated, which anion is readily soluble in water with metallic ions in the solutions, and which anion forms conjugate acids that are strong acids; wherein said basic aluminum material is characterized by:

(a) size exclusion high performance liquid chromatography peaks corresponding to peak 3 and peak 4 of size exclusion chromatograms formed by HPLC technique; and (b) at least 25% by weight of the basic aluminum material being in the form of $Al_6$ polyhydroxyaquoaluminum species; and (2) an antiperspirant active material containing a metal cation selected from the group consisting of Zr, Hf, Ti and Sn.

22. An antiperspirant active composition according to claim 21, wherein the composition further includes a neutral amino acid.

23. A method of forming an antiperspirant active composition according to claim 14, wherein said mixing is performed without heating.

24. A method of forming an antiperspirant active composition according to claim 16, wherein each of said antiperspirant active material and said basic aluminum material is in aqueous solution during said mixing, and wherein said basic aluminum material is in aqueous solution after said step (b'), the basic aluminum material in aqueous solution after said step (b') not being diluted prior to mixing.

25. A method of forming an antiperspirant active composition according to claim 24, wherein said mixing is performed without heating.

* * * * *